United States Patent [19] [11] 4,202,894

Pfiffner [45] May 13, 1980

[54] PIPERIDINES MORPHOLINES, ETC., AND FUNGICIDAL COMPOSITIONS THEREOF

[75] Inventor: Albert Pfiffner, Bulach, Switzerland

[73] Assignee: Hoffmann-La Roche Inc., Nutley, N.J.

[21] Appl. No.: 852,768

[22] Filed: Nov. 18, 1977

[30] Foreign Application Priority Data

Nov. 22, 1976 [AT] Austria ............................ A 8660/76

[51] Int. Cl.[2] ..................... C07D 295/02; A01N 9/22; C07D 211/14

[52] U.S. Cl. ................................. 424/248.4; 424/258; 424/267; 544/105; 544/173; 544/178; 546/141; 546/149; 546/153; 546/164; 546/165; 546/150; 546/192; 542/429; 542/469

[58] Field of Search ...................... 260/293.65, 293.72; 544/105, 178, 173; 546/141, 149, 153, 165, 164, 192, 150; 424/248, 267, 258; 542/429, 469

[56] References Cited

U.S. PATENT DOCUMENTS

| | | | |
|---|---|---|---|
| 2,213,469 | 9/1940 | Leffler | 544/178 |
| 2,647,122 | 7/1953 | Archer et al. | 260/293.65 |
| 2,662,886 | 12/1953 | Ruddy et al. | 260/293.72 |
| 4,104,383 | 8/1978 | Krausz | 544/178 |

FOREIGN PATENT DOCUMENTS

| | | |
|---|---|---|
| 1164152 | 9/1964 | Fed. Rep. of Germany . |
| 1173722 | 1/1965 | Fed. Rep. of Germany . |
| 1198125 | 8/1965 | Fed. Rep. of Germany . |
| 1320244 | 1/1963 | France . |
| 92920 | 10/1972 | German Democratic Rep. . |
| 116739 | 12/1975 | German Democratic Rep. . |
| 7713685 | 12/1967 | Netherlands . |

OTHER PUBLICATIONS

Cannata et al., "Tetrahedron", vol. 27, pp. 5247–5254, (1971).

*Primary Examiner*—Alan L. Rotman
*Assistant Examiner*—Robert T. Bond
*Attorney, Agent, or Firm*—Jon S. Saxe; George M. Gould; Peter R. Shearer

[57] ABSTRACT

Heterocyclic compounds characterized by the formula

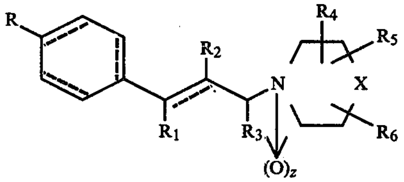

I wherein R, $R_1$, $R_2$, $R_3$, $R_4$, $R_5$, $R_6$, X and z are as hereinafter set forth, prepared, inter alia, by reacting a compound characterized by the formula

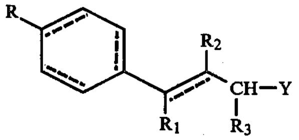

II with an amine characterized by the formula

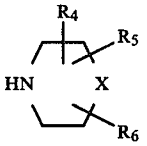

III wherein R, $R_1$, $R_2$, $R_3$, $R_4$, $R_5$, $R_6$, X and Y are as hereinafter set forth, are described. The end products are useful as fungicidal agents.

140 Claims, No Drawings

PIPERIDINES MORPHOLINES, ETC., AND FUNGICIDAL COMPOSITIONS THEREOF

BRIEF SUMMARY OF THE INVENTION

The invention relates to heterocyclic compounds of the formula

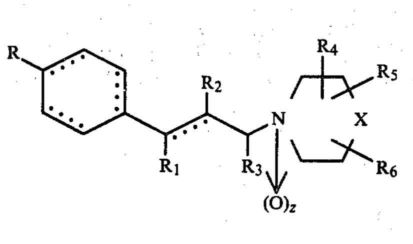
I wherein R, $R_1$, $R_2$, $R_3$, $R_4$, $R_5$, $R_6$, X and z are as hereinafter described.

In another aspect, the invention relates to fungicidal compositions and methods.

In yet another aspect, the invention relates to compounds useful as intermediates.

DETAILED DESCRIPTION OF THE INVENTION

The present invention comprises heterocyclic compounds of the formula

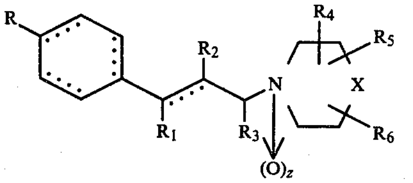
I wherein R is alkyl of 4 to 12 carbon atoms, cycloalkyl of 3 to 7 carbon atoms, mono(lower alkyl)-substituted cycloalkyl of 4 to 7 carbon atoms, cycloalkylalkyl of 4 to 12 carbon atoms, phenyl or aryl-(lower alkyl) of 7 to 12 carbon atoms; $R_1$, $R_2$ and $R_3$, independently, are hydrogen or alkyl of 1 to 8 carbon atoms; $R_4$, $R_5$ and $R_6$, independently, are hydrogen or alkyl of 1 to 8 carbon atoms, and two of $R_4$, $R_5$ and $R_6$ can each be bonded to the same carbon atom or together can form a fused alicyclic or aromatic 6-membered ring; provided that when R is tert.-butyl, at least one of $R_1$ and $R_3$ is alkyl of 2 to 8 carbon atoms or $R_2$ is hydrogen or alkyl of 2 to 8 carbon atoms or at least one of $R_4$, $R_5$ and $R_6$ is alkyl of 5 to 8 carbon atoms; X is methylene or an oxygen atom; z is zero or 1 and the dotted bonds can be hydrogenated, and acid addition salts of those compounds of formula I which are basic.

Unless stated to the contrary, the term "lower alkyl" as used herein denotes a straight-chain or branched-chain hydrocarbon group of 1 to 4 carbon atoms, such as, methyl, ethyl, propyl, isopropyl, butyl, isobutyl and tert.-butyl. Alkyl groups of 4 to 12 carbon atoms are straight-chain or branched-chain hydrocarbon groups, for example, butyl, isobutyl, tert.-butyl, neopentyl, 1,1-dimethylpropyl, 1,1-dimethylpentyl, 1,1-diethylpropyl, 1,1-dimethylbutyl, 1-isopropyl-3-methyl-but-1-yl, 1-ethyl-1-methylbutyl, dodecyl, and the like. The term "cycloalkylalkyl" includes, in particular, those groups in which the alkyl moiety is branched. The term "aryl-(lower alkyl)" includes not only groups which are mono- or di(lower alkyl)-substituted in the aryl ring but also groups which are mono- or di(lower alkyl)-substituted in the lower alkyl moiety. Exemplary of aryl(-lower alkyl) groups are benzyl, phenylethyl, (lower alkyl)-benzyl, for example, methylbenzyl and dimethylbenzyl, naphthylmethyl, 2-phenyl-propan-2-yl, 1 -phenyl-1-ethyl, or the like.

Compounds of formula I which are basic form salts with organic and inorganic acids. Preferred salts are those formed with physiologically acceptable acids, including, in particular, the salts formed with hydrohalic acids, for example, hydrochloric acid and hydrobromic acid, phosphoric acid, nitric acid, monofunctional and bifunctional carboxylic acids and hydroxycarboxylic acids, for example, acetic acid, maleic acid, succinic acid, fumaric acid, tartaric acid, citric acid, salicylic acid, sorbic acid and lactic acid, and sulfonic acids, for example, 1,5-naphthalene-disulfonic acid. Salts of this type are prepared in a known manner.

The compounds of formula I and acid addition salts of those compounds which are basic can be prepared by (a) reacting a halide of the formula

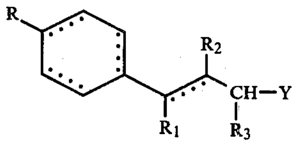
II wherein R, $R_1$, $R_2$, $R_3$ and the dotted bonds are as previously described, and Y is chlorine, bromine or iodine, with an amine of the formula

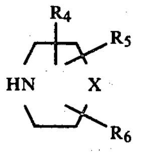
III wherein $R_4$, $R_5$, $R_6$ and X are as previously described, or (b) catalytically hydrogenating or reducing with formic acid the aliphatic double bond in a compound of the formula

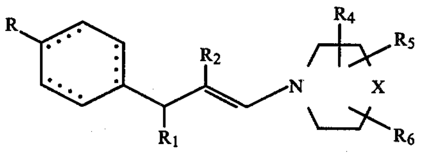
IV.

wherein R, $R_1$, $R_2$, $R_4$, $R_5$, $R_6$, X and the dotted bonds are as previously described, or (c) reacting a compound of the formula

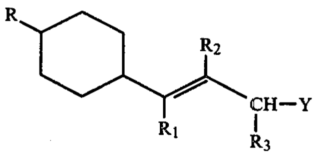
V wherein R, $R_1$, $R_2$, $R_3$ and Y are as previously described, with an amine of formula III, or (d) catalytically hydrogenating a compound of the formula

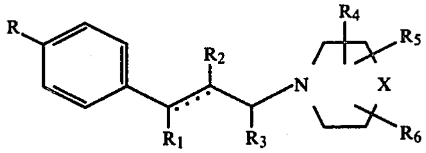

VI wherein R, $R_1$, $R_2$, $R_3$, $R_4$, $R_5$, $R_6$, X and the dotted bond are as previously described, or (e) treating a compound of the formula

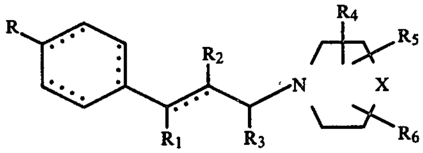

VII wherein R, $R_1$, $R_2$, $R_3$, $R_4$, $R_5$, $R_6$, X and the dotted bonds are as previously described, with hydrogen peroxide or a peracid, or (f) converting a compound of formula I which is basic into a salt with an acid in a known manner.

The Roman numerals mentioned in the following text relate to the structural formulas given earlier and/or to the structural formulas given in the following Formula Schemes and/or to the structural formulas given in the description in connection with the preparation of the starting materials. Some of the formulas given in the text are elaborated in Formula Schemes A and B. Thus, for example, formula I hereinbefore includes all of the formulas given in Formula Scheme A with the exception of formulas IIa, IIb and IV. In Formula Schemes A and B, the symbols R, $R_1$, $R_2$, $R_3$, $R_4$, $R_5$, $R_6$, X and Y and the dotted bonds are as previously described. In Formula Scheme B, Et is ethyl and Ac is acetyl.

Formula Scheme A

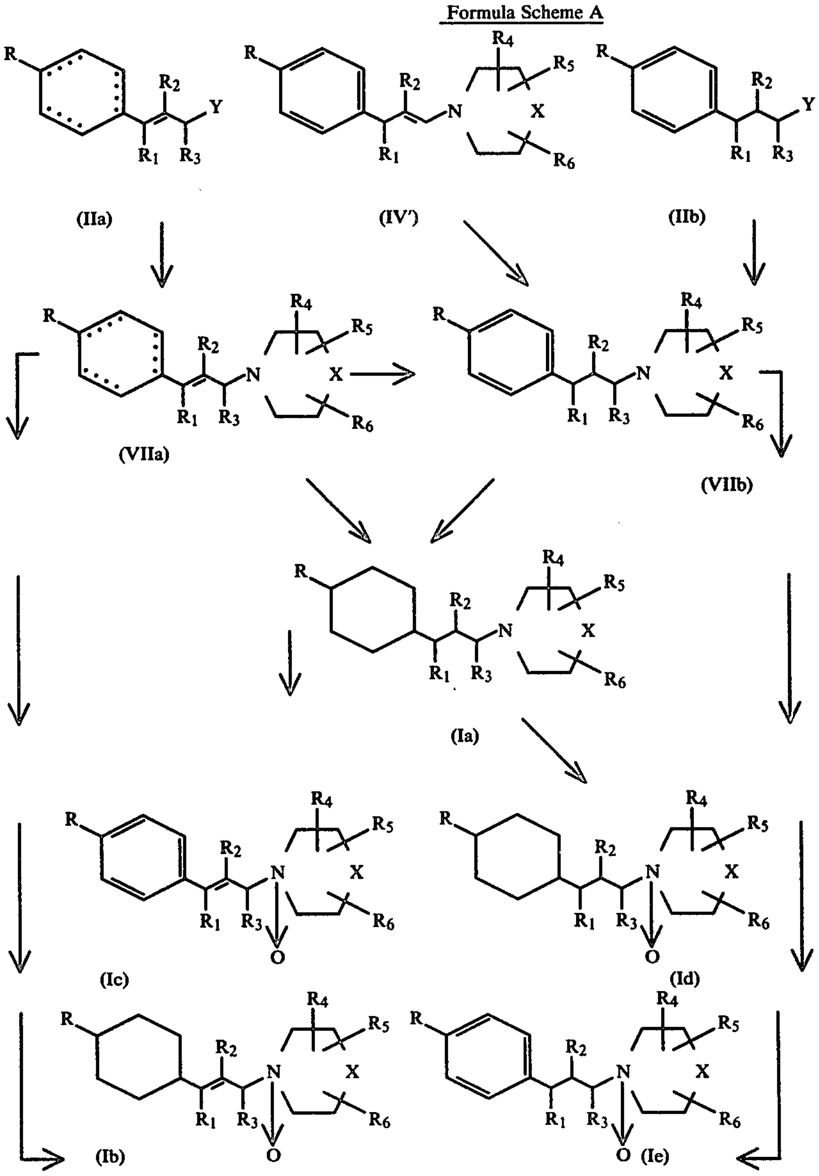

(IIa) (IV') (IIb) (VIIa) (VIIb) (Ia) (Ic) (Id) (Ib) (Ie)

Formula Scheme B
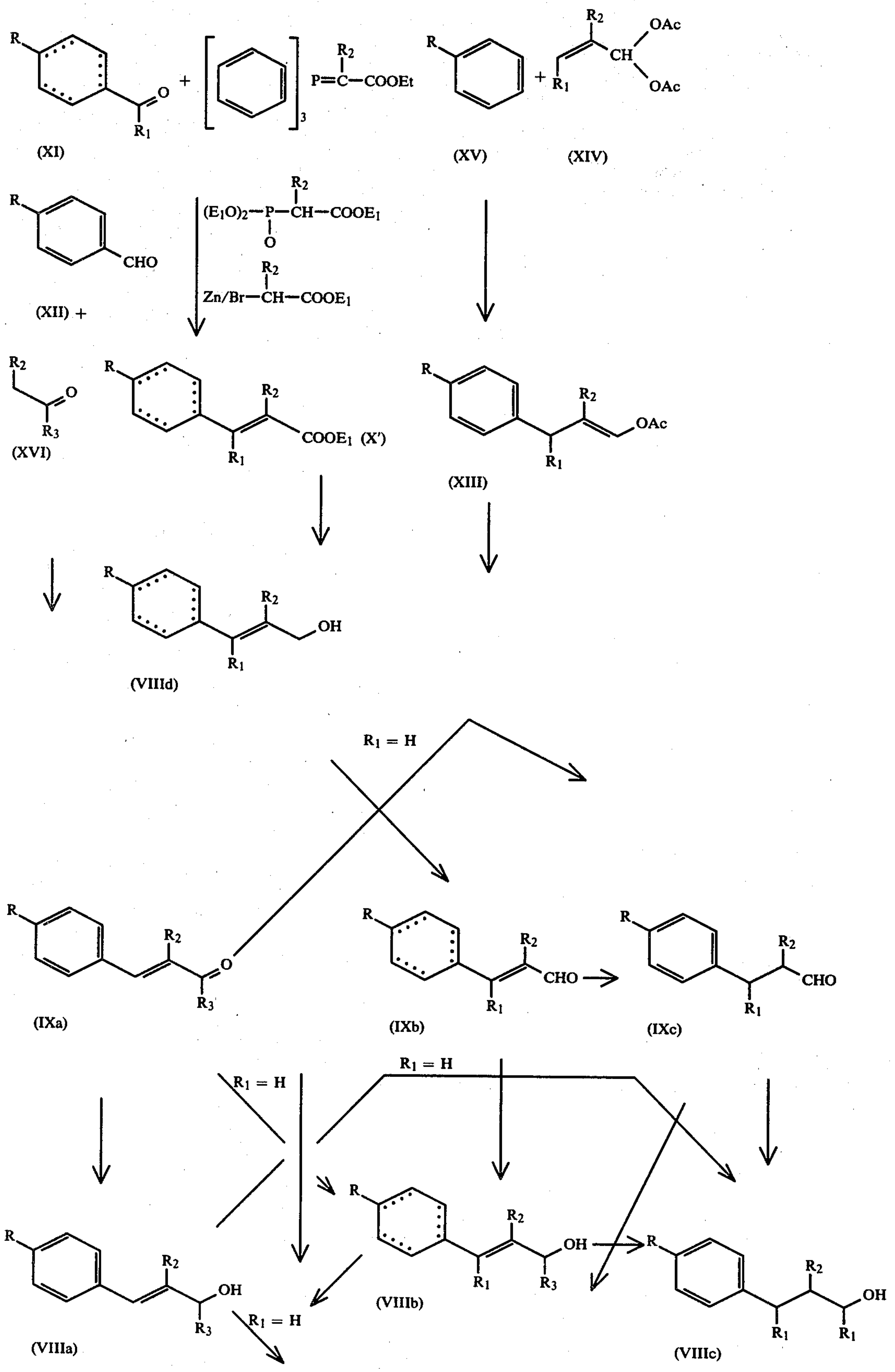
(XI) (XV) (XIV) (XII) + (XVI) (X') (XIII) (VIIId) (IXa) (IXb) (IXc) (VIIIa) (VIIIb) (VIIIc)

-continued

Formula Scheme B

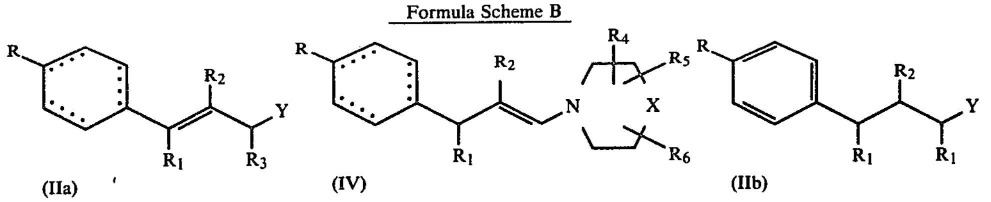

(IIa) (IV) (IIb)

According to process embodiment (a), a halide of formula II is reacted with an amine of formula III in an inert solvent, preferably an ether, such as, diethyl ether, tetrahydrofuran or dioxane, in the presence of a base, for example, triethylamine or an excess of the amine of formula III.

When a halide of formula IIa is used as the starting material, diethyl ether is preferably used as the inert solvent. A particularly suitable reaction temperature lies in the range of from about 0° C. to about the reflux temperature of the reaction mixture. The reaction is preferably carried out at the boiling point of the reaction mixture.

When a halide of formula IIb is reacted with an amine of formula III, a high boiling alcohol is preferably used as the inert solvent. Ethylene glycol or glycerol is particularly preferred. The reaction is preferably carried out at a temperature in the range of from about 50° C. to about 150° C. In a particularly preferred aspect, the reaction is carried out using ethylene glycol as the inert solvent and at a temperature of 100°-110° C.

According to process embodiment (b), a compound of formula IV is catalytically hydrogenated or is reduced with formic acid. Particularly suitable catalysts are noble metal catalysts, for example, platinum, palladium (optionally precipitated onto charcoal) and Raney nickel. Palladium-on-charcoal is the preferred catalyst. Suitable inert solvents for the catalytic hydrogenation are hydrocarbons, such as, benzene, toluene or xylene, and alcohols, such as, methanol or ethanol. Toluene is the preferred inert solvent. The catalytic hydrogenation is advantageously carried out at a temperature in the range of from about 0° C. to about 50° C., preferably at room temperature. The reduction of a compound of formula Iv with formic acid is preferably carried out in the absence of a solvent. Formic acid is added dropwise to a compound of formula IV at a temperature in the range of from about 0° C. to about 100° C., preferably at 50° to 70° C., if necessary while cooling.

According to process embodiment (c), a compound of formula V is reacted with an amine of formula III under the conditions described earlier in connection with process embodiment (a).

According to process embodiment (d), a compound of formula VI is catalytically hydrogenated. Platinum or palladium is preferably used as the catalyst, with water or alcohol being used as the solvent. In order to avoid a possible hydrogenolysis, at least one equivalent of acid, preferably hydrochloric acid, is added to the catalytic hydrogenation mixture. When a perhydrogenation is desired, the catalytic hydrogenation is carried out utilizing platinum in glacial acetic acid with the addition of perchloric acid. The aromatic ring is completely hydrogenated under these conditions.

According to process embodiment (e), a compound of formula VII is treated with hydrogen peroxide or a peracid. When a compound of formula Ia, VIIa or VIIb (see Formula Scheme A) is used as the starting material, the treatment is carried out with hydrogen peroxide. In this case, an alcohol, such as, methanol, ethanol or isopropanol, is used as the solvent, with isopropanol being preferred. The treatment with hydrogen peroxide is preferably carried out at a temperature in the range of from about 0° C. to about 50° C., especially at 40° C. When a compound of formula Ia or VIIb is used as the starting material, the treatment is preferably carried out with a peracid, such as peracetic acid, perbenzoic acid, m-chloroperbenzoic acid, peradipic acid, etc., or with hydrogen peroxide in a corresponding acid or acid anhydride. A halogenated hydrocarbon, such as, methylene chloride, chloroform or ethylene chloride, is preferably used as the solvent when a peracid is used. Suitable treatment temperatures are the same as those mentioned earlier in connection with the treatment with hydrogen peroxide.

A preferred class of compounds of formula I comprises those wherein R is 1,1-dimethylpropyl. Also preferred are those compounds of formula I wherein R is phenyl.

Preferred compounds of formula I are:

1-[3-(p-Tert.amyl-phenyl)-2-methyl-propyl]-piperidine,

1-[3-(p-tert.amyl-phenyl)-2-methyl-propyl]-3-methyl-piperidine,

1-[3-(p-tert.amyl-phenyl)-2-methyl-propyl]-3,5-dimethyl-piperidine,

4-[3-(p-tert.amyl-phenyl)-2-methyl-propyl]-2,6-dimethyl-morpholine,

1-[3-(4-tert.amyl-cyclohexyl)-2-methyl-propyl]-piperidine,

1-[3-(4-tert.amyl-cyclohexyl)-2-methyl-propyl]-3-methyl-piperidine,

1-[3-(4-tert.amyl-cyclohexyl)-2-methyl-propyl]-3,5-dimethyl-piperidine,

4-[3-(4-tert.amyl-cyclohexyl)-2-methyl-propyl]-2,6-dimethyl-morpholine,

4-[3-(4-tert.amyl-cyclohexyl)-2-methyl-2-propenyl]-2,6-dimethyl-morpholine,

1-[3-(4-tert.amyl-cyclohexyl)-2-methyl-2-propenyl]-piperidine,

1-[3-(4-tert.amyl-cyclohexyl)-2-methyl-2-propenyl]-3-methyl-piperidine,

1-[3-(4-tert.amyl-cyclohexyl)-2-methyl-2-propenyl]-3,5-dimethyl-piperidine,

1-[3-(p-tert.amyl-phenyl)-2,3-dimethyl-2-propenyl]-piperidine,

1-[3-(p-tert.amyl-phenyl)-2,3-dimethyl-2-propenyl]-3-methyl-piperidine,

1-[3-(p-tert.amyl-phenyl)-2,3-dimethyl-2-propenyl]-3,5-dimethyl-piperidine,

4-[3-(p-tert.amyl-phenyl)-2,3-dimethyl-2-propenyl]-2,6-dimethyl-morpholine,

1-[3-(p-tert.amyl-phenyl)-2,3-dimethyl-propyl]-piperidine,

1-[3-(p-tert.amyl-phenyl)-2,3-dimethyl-propyl]-3-methyl-piperidine,

1-[3-(p-tert.amyl-phenyl)-2,3-dimethyl-propyl]-3,5-dimethyl-piperidine,
4-[3-(p-tert.amyl-phenyl)-2,3-dimethyl-propyl]-2,6-dimethyl-morpholine,
1-[3-[p-(1,1-diethyl-propyl)-phenyl]-2-methyl-propyl]-3-methyl-piperidine,
1-[3-[p-(1,1-dimethyl-pentyl)-phenyl]-2-methyl-propyl]-3-methyl-piperidine,
1-[3-[p-(1,1-dimethyl-pentyl)-phenyl]-2-methyl-propyl]-piperidine,
4-[3-(4-biphenylyl)-2-methyl-propyl]-2,6-dimethyl-morpholine,
1-[3-[p-(α,α-dimethyl-benzyl)-phenyl]-2-methyl-propyl]-piperidine,
1-[3-[p-(α,α-dimethyl-benzyl)-phenyl]-2-methyl-propyl]-3-methyl-piperidine,
1-[3-[p-(α,α-dimethyl-benzyl)-phenyl]-2-methyl-propyl]-3,5-dimethyl-piperidine,
4-[3-[p-(α,α-dimethyl-benzyl)-phenyl]-2-methyl-propyl]-2,6-dimethyl-morpholine,
1-[3-[p-(α,α-dimethyl-benzyl)-phenyl]-2,3-dimethyl-2-propenyl]-3,5-dimethyl-piperidine,
1-[3-[p-(α,α-dimethyl-benzyl)-phenyl]-2,3-dimethyl-propyl]-3,5-dimethyl-piperidine,
1-[3-[4-(1-cyclohexyl-1-methyl-ethyl)-cyclohexyl]-2-methyl-propyl]-piperidine,
4-[3-[4-(1-cyclohexyl-1-methyl-ethyl)-cyclohexyl]-2-methyl-propyl]-2,6-dimethyl-morpholine,
1-[3-[p-(1-cyclohexyl-1-methyl)-phenyl]-2-methyl-propyl]-piperidine,
1-[3-[p-(1-cyclohexyl-1-methyl)-phenyl]-2-methyl-propyl]-3,5-dimethyl-piperidine and
4-[3-[p-(1-cyclohexyl-1-methyl)-phenyl]-2-methyl-propyl]-2,6-dimethyl-morpholine.

Some of the starting materials of formulas II, IV, V, VI and VII are novel.

The compounds of formulas VI and VII are prepared by alkylating an amine of formula III with a halide of formula II or V. The alkylation is carried out in the same manner as described earlier in connection with process embodiment (a).

The halides can be prepared in a known manner from a corresponding alcohol of the formula

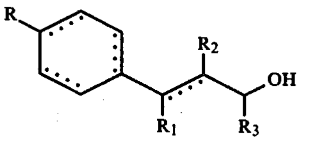
VIII or

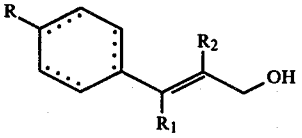
VIIId wherein R, $R_1$, $R_2$ and $R_3$ and the dotted bonds are as previously described,
by treatment with a phosphorus halide, such as, phosphorus tribromide, phosphorus trichloride, phosphorus pentabromide or phosphorus pentachloride, with or without the addition of a tertiary base.

An alcohol of formula VIII or VIIId is obtained in a known manner from a compound of the formula

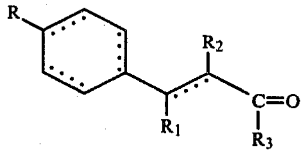
IX or

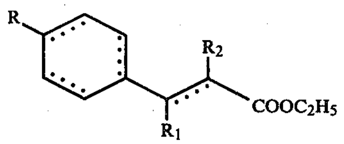
X wherein R, $R_1$, $R_2$, $R_3$ and the dotted bonds are as previously described,
by reduction with a suitably complex hydride. Suitable complex hydrides for the reduction of a compound of formula IX are, for example, borohydrides, such as, sodium borohydride, or alanates, such as, lithium aluminum hydride. Lithium aluminum hydride is suitable for the reduction of a compound of formula X.

The compounds of formulas IX and X are obtained from an aldehyde or ketone of the formula

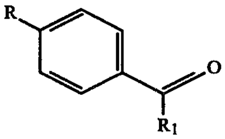

wherein R, $R_1$ and the dotted bonds are as previously described,
by means of a Wittig reaction, Horner reaction or Reformatzky reaction (see Formula Scheme B).

Synthesis (1974), page 122 et seq. is referred to as exemplifying the Wittig reaction and the Horner reaction. The relevant secondary literature is also cited in this literature reference. Examples of the Reformatzky reaction are described in Bull. Soc. Chim. France (1961), page 2145 et seq. A detailed bibliography for the Reformatzky reaction is also given in this literature reference.

In order to prepare a compound of formula IXa, wherein $R_2$ and $R_3$, individually, are alkyl, or $R_2$ is alkyl and $R_3$ is hydrogen, the aldehyde of formula XII is reacted with a ketone or aldehyde of formula XVI under the conditions of a Claisen-Schmidt condensation in a known manner. The relevant literature is given in "Namenreaktionen der organischen Chemie", Dr. Alfred Huthig Verlag GmbH, Heidelberg 1961, page 94.

A compound of formula IXc is prepared from a compound of formula XIII by saponification in a known manner. The saponification is carried out, for example, as described in Bull. Soc. Chim. France (1961), page 1194 et seq. A compound of formula XIII is prepared from the compound of formula XV and a compound of formula XIV by a Friedel-Crafts reaction, also in a known manner. The Friedel-Crafts reaction can be carried out, for example, in an analogous manner to the examples which are given in the aforementioned literature reference.

A compound of formula VIIId is oxidized to a compound of formula IXb in a known manner. For example, the methods described in J. Org. Chem., 39, 3304 (1974) can be utilized.

A compound of formula IXb or IXc can be converted into a compound of formula VIIIb or VIIIc in a known manner by means of a Grignard reaction. When $R_3$, in a compound of formula IXa, is hydrogen, a compound of formula VIIIb, wherein $R_3$ is other than hydrogen, is also obtained by means of a Grignard reaction. With respect to the Grignard reaction, the monograph "Grignard Reactions of Nonmetallic Substrates", Verlag Prentice-Hall Inc., New York, 1954, is referred to.

A compound of formula IXa, IXb, VIIIa or VIIIb is converted into a compound of formula IXc or VIIIc in a known manner by dissolution in an alcohol, preferably methanol or ethanol, optionally with the addition of water and water-soluble inorganic bases, for example, sodium carbonate, potassium carbonate or calcium hydroxide, and hydrogenation at room temperature in the presence of palladium/charcoal.

A compound of formula IV (see Formula Scheme B) is prepared from an aldehyde of formula IXc by reaction with an amine of formula III. For this purpose, an excess of the amine of formula III is added to the aldehyde and the mixture is heated under reflux in benzene or toluene, the water which forms distilled azeotropically (see "Advances in Organic Chemistry", Vol. 4, pp. 9 et seq., Verlag Interscience Publishers, New York, London, 1963).

Preferred starting materials of formula IXb and IXc hereinbefore are:

p-Tert.amyl-α,β-dimethyl-cinnamaldehyde,
p-(α,α-dimethyl-benzyl)-α,β-dimethyl-cinnamaldehyde,
3-(p-isobutyl-phenyl)-2-methyl-propionaldehyde,
3-(p-neopentyl-phenyl)-2-methyl-propionaldehyde,
3-(p-tert.-amyl-phenyl)-2-methyl-propionaldehyde,
3-[p-(1,1-dimethyl-pentyl)-phenyl]-2-methyl-propionaldehyde,
3-[p-(1,1-diethyl-propyl)-phenyl]-2-methyl-propionaldehyde,
3-(p-tert.butyl-phenyl)-2-ethyl-propionaldehyde,
3-(p-tert.butyl-phenyl)-2-isopropyl-propionaldehyde,
3-(p-cyclohexyl-phenyl)-2-methyl-propionaldehyde,
3-(p-biphenylyl)-2-methyl-propionaldehyde,
3-(p-tert.butyl-phenyl)-2-octyl-propionaldehyde,
3-[p-(1-propyl-1-methyl-pentyl)-phenyl]-2-methyl-propionaldehyde,
3-[p-(1-ethyl-1-methyl-butyl)-phenyl]-2-methyl-propionaldehyde,
3-[p-(1,2-dimethyl-propyl)-phenyl]-2-methyl-propionaldehyde,
3-[p-(1-isopropyl-3-methyl-butyl)-phenyl]-2-methyl-propionaldehyde,
3-[p-(α,α-dimethyl-benzyl)-phenyl]-2-methyl-propionaldehyde,
3-[4-cyclohexyl-1-methyl-ethyl)-cyclohexyl]-2-methyl-propionaldehyde and
3-[p-(1-cyclohexyl-1-methyl)-phenyl]-2-methyl-propionaldehyde.

Preferred starting materials of formula IIa hereinbefore are:

3-(p-Tert.amyl-phenyl)-1-methyl-allyl bromide,
3-(p-tert.amyl-phenyl)-2-methyl-allyl bromide,
3-(p-tert.amyl-phenyl)-3-methyl-allyl bromide,
3-(p-tert.amyl-phenyl)-1,2-dimethyl-allyl bromide,
3-(p-tert.amyl-phenyl)-1,3-dimethyl-allyl bromide,
3-(p-tert.amyl-phenyl)-2,3-dimethyl-allyl bromide,
3-(p-tert.amyl-phenyl)-1,2,3-trimethyl-allyl bromide,
3-(4-tert.amyl-cyclohexyl)-2-methyl-allyl bromide, and
3-[p-(α,α-dimethyl-benzyl)-phenyl]-2,3-dimethyl-allyl bromide.

Preferred starting materials of formula IIb hereinbefore are:

3-(p-tert.amyl-phenyl)-1-methyl-propyl bromide,
3-(p-tert.amyl-phenyl)-2-methyl-propyl bromide,
3-(p-tert.amyl-phenyl)-3-methyl-propyl bromide,
3-(p-tert.amyl-phenyl)-1,2-dimethyl-propyl bromide,
3-(p-tert.amyl-phenyl)-1,3-dimethyl-propyl bromide,
3-(p-tert.amyl-phenyl)-2,3-dimethyl-propyl bromide,
3-(p-tert.amyl-phenyl)-1,2,3-trimethyl-propyl bromide,
3-(p-tert.amyl-phenyl)-2-methyl-propyl bromide and
3-[p-(α,α-dimethyl-benzyl)-phenyl]-2,3-dimethyl-propyl bromide.

Preferred starting materials of formula IV hereinbefore are:

1-[3-(p-Tert.-amyl-phenyl)-2-methyl-1-propenyl]-piperidine,
1-[3-(p-tert.amyl-phenyl)-2-methyl-1-propenyl]-3-methyl-piperidine,
1-[3-(p-tert.amyl-phenyl)-2-methyl-1-propenyl]-3,5-dimethyl-piperidine,
4-[3-(p-tert.amyl-phenyl)-2-methyl-1-propenyl]-2,6-dimethyl-morpholine,
1-[3-[p-(1,1-diethyl-propyl)-phenyl]-2-methyl-1-propenyl]-3-methyl-piperidine,
1-[3-[p-(1,1-dimethyl-propyl)-phenyl]-2-methyl-1-propenyl]-3-methyl-piperidine,
1-[3-[p-(1,1-dimethyl-propyl)-phenyl]-2-methyl-1-propenyl]piperidine,
4-[3-(4-biphenyl)-2-methyl-1-propenyl]-2,6-dimethyl-morpholine,
1-[3-[p-(α,α-dimethyl-benzyl)-phenyl]-2-methyl-1-propenyl]-piperidine,
1-[3-[p-(α,α-dimethyl-benzyl)-phenyl]-2-methyl-1-propenyl]-3-methyl-piperidine,
1-[3-[p-(α,α-dimethyl-benzyl)-phenyl]-2-methyl-1-propenyl]-3,5-dimethyl-piperidine,
4-[3-[p-(α,α-dimethyl-benzyl)-phenyl]-2-methyl-1-propenyl]-2,6-dimethyl-morpholine,
1-[3-[p-(1-cyclohexyl-1-methyl)-phenyl]-2-methyl-1-propenyl]-piperidine,
1-[3-[p-(1-cyclohexyl-1-methyl)-phenyl]-2-methyl-1-propenyl]-3,5-dimethyl-piperidine and
4-[3-[p-(1-cyclohexyl-1-methyl)-phenyl]-2-methyl-1-propenyl]-2,6-dimethyl-morpholine.

It is not necessary to isolate the compounds of formula IV. Such compounds can be converted directly into compounds of formula VIIb, without working up, either by adding formic acid or by hydrogenation.

The compounds of formula I possess fungicidal activity and can, accordingly, be used for combatting fungi in agriculture and in horticulture. The compounds are particularly suitable for combatting powdery mildew fungi such as, for example, *Erysiphe graminis* (powdery mildew of cereals), *Erysiphe cichoracearum* (powdery mildew of cucumbers), *Podosphaera leucotricha* (powdery mildew of apples), *Sphaerotheca pannosa* (powdery mildew of roses) and *Oidium tuckeri* (powdery mildew of vines), rust diseases, for example, those of the genera Puccinia, Uromyces and Hemileia, especially *Puccinia graminis* (stem rust of cereals), *Puccinia coronata* (crown rust of oats), *Puccinia sorghi* (corn rust), *Puccinia striiformis* (stripe rust of wheat), *Puccinia recondita* (leaf rust of cereals), *Uromyces fabae* and *appendiculatus* (bean rusts), as well as *Hemileia vastatrix* (coffee rust) and *Phragmidium mucronatum* (leaf rust of roses).

Furthermore, the compounds of formula I are also active against the following phytopathogenic fungi:

*Ustilago avenae* (loose smut of oats), *Venturia inaequalis* (apple scab), *Cercospora arachidicola* (peanut early leaf spot), *Ophiobolus graminis* (cereal take-all), *Septoria nodorum* (cereal leaf spot) or *Marssonina rosae* (rose blackspot). The compounds of formula I possess pronounced subsidiary activity against various species of the following genera: Rhizoctonia, Tilletia and Helminthosporium, and also, in part, against Peronospora, Coniophora, Lenzites, Corticium, Thielaviopsis and Fusarium.

Furthermore, compounds of formula I are also active against phythopathogenic bacteria, for example, *Xanthomonas vesicatoria, Xanthomonas oryzae* and other Xanthomonades as well as against various species of Erwinia, such as, *Erwinia tracheiphila.*

The compounds of formula I are also active as insecticides and acaricides, and, to some extent, insect growth-regulating effects and anti-feedant effects are also found. Thus, for example, 1-{3-[(1-isopropyl-3-methyl-butyl)-phenyl]-2-methyl-propyl}-3,4-dimethyl-piperidine showed a 100% activity in the larvicide test with *Adoxophyes orana* at a dosage of $10^{-6}$ g/cm$^2$ and a 50% activity at a dosage of $10^{-7}$ g/cm$^2$.

As will be evident from the following biological tests, the compounds of formula I are active under greenhouse conditions even at a concentration of as little as 5 mg. to 500 mg. of active ingredient, that is, a compound of formula I, per liter of spray liquor. In the open, concentrations of 100 g to 2,500 g. of active ingredient per hectare and per treatment are advantageously utilized. For example, in order to combat powdery mildew of cereals successfully, it is advantageous to use a concentration of 200 g. to 1,000 g., preferably 200 g. to 600 g., of active ingredient per hectare and per application. For combatting cereal rust, it is advantageous to use concentrations of 500 g. to 2,500 g. and particularly preferably, in the case of the most active members, 500 g. to 2,000 g., of active ingredient per hectare and per application.

Some of the compounds of formula I display a high systemic activity. Untreated parts of the plants can also be protected as a result of secondary distribution of the active ingredient (gas phase action).

For practical purposes, the compounds of formula I can be said to be substantially non-toxic to vertebrates. The toxicity of the compounds of formula I is on average above 1,000 mg. per kg. of body weight in the acute toxicity test on mice. Individual members show $LD_{50}$ values, determined on mice, in the range of from about 400 to about 1,000 mg. per kg. of body weight, while other members show $LD_{50}$ values which are in the range of from about 1,000 to about 10,000 mg. per kg. of body weight in the acute toxicity test on mice.

The biological tests described hereinafter illustrate the activity of the compounds of formula I, the results are summarized in the Tables which follow.

(a) *Erysiphe graminis*

30–40 barley seedlings of the HERTA variety (distributed on 2 pots of 7 cm diameter), the seedlings being in each case in the one-leaf stage, were thoroughly sprayed from all sides with an aqueous dispersion of the test substance (processed in the usual manner as a sprayable powder) and were then grown in a greenhouse at 22°–26° C. and 80% relative atmospheric humidity with a light period of 16 hours. The infection was effected 2 days after the treatment by dusting the test plants with conidia of *Erysiphe graminis.* 7 days after the infection, the leaf surface infected by *Erysiphe graminis* was determined in % relative to the leaf surface of the infected untreated control. The results are summarized in Table I hereinafter.

(b) *Puccinia coronata*

30–40 oat seedlings of the FLAEMINGSKRONE variety (distributed on 2 pots of 7 cm diameter), each seedling being in the one-leaf stage, were thoroughly sprayed from all sides with an aqueous dispersion of the test substance (processed in the usual manner as a sprayable powder) and were then grown in a climatically controlled chamber at 17° C. and 70–80% relative atmospheric humidity with a light period of 16 hours. After 2 days, the test plants were infected by spraying with uredospores (300,000 spores/ml) of *Puccinia coronata* suspended in distilled water. The plants were then incubated in the dark for 24 hours at 20° C. and an atmospheric humidity above 90%, and were subsequently moved into a greenhouse at a temperature of 22°–26° C. and a relative atmospheric humidity of 70% with a light period of 18 hours. On the 9th day after infection, the leaf surface infected by *Puccinia coronata* was determined in % relative to the infected untreated control. The results are summarized in Table I hereinafter.

(c) *Venturia inaequalis*

3 small apple plants (distributed in 3 pots of 5 cm diameter) raised from seeds of the GOLDEN DECICIOUS variety, the plants being in the 4- to 5-leaf stage, were thoroughly sprayed on all sides with an aqueous dispersion on the test substance (processed in the usual manner as a sprayable powder). The treated plants were then grown for 2 days at 17° C. and 70–80% relative atmospheric humidity with a light period of 14 hours. Thereafter, the plants were infected by spraying with a suspension of conidia of *Venturia inaequalis* in distilled water (200,000 conidia/ml). After the infection, the plants were incubated in the dark for 48 hours at 16°–18° C. and a relative atmospheric humidity of above 90%, and were then moved to a shaded greenhouse at a temperature of 22°–26° C. and a relative atmospheric humidity of above 80%. On the 13th day after the infection, the leaf surface infected by *Venturia inaequalis* was determined relative to that of the infected untreated control. The results are summarized in Table II hereinafter.

Table I

| Test substance | Concentration (in mg/l of spray liquor) | Activity (in %) *Erysiphe graminis* | Activity (in %) *Puccinia coronta* |
|---|---|---|---|
| 1-[3-[p-(1,1-Diethyl-propyl)-phenyl]-2-methyl-propyl]-piperidine | 500 | 100 | |
| | 160 | 100 | 100 |
| | 50 | 97 | 50 |
| | 16 | 85 | 10 |
| | 5 | 55 | 0 |
| 1-[3-[p-(1,1-Diethyl-propyl)-phenyl]-2-methyl-propyl]-3-methyl-piperidine | 500 | 100 | 100 |
| | 160 | 100 | 100 |
| | 50 | 100 | 90 |
| | 16 | 95 | 10 |
| | 5 | 75 | 0 |
| 1-[3-(p-Tert.amyl-phenyl)-2-methyl-propyl]-piperidine | 500 | 100 | 100 |
| | 160 | 100 | 98 |
| | 50 | 100 | 87 |
| | 16 | 90 | 20 |
| | 5 | 85 | 10 |
| 1-[3-(p-Tert.amyl-phenyl)-2-methyl-propyl]-3-methyl-piperidine | 500 | 100 | 100 |
| | 160 | 100 | 100 |
| | 50 | 100 | 93 |
| | 16 | 95 | 40 |
| | 5 | 60 | 0 |
| 1-[3-[p-(1,1-Dimethyl-pentyl)- | 500 | 100 | 100 |
| | 160 | 100 | 35 |

Table I-continued

| Test substance | Concentration (in mg/l of spray liquor) | Activity (in %) *Erysiphe graminis* | *Puccinia coronta* |
|---|---|---|---|
| phenyl]-2-methyl- | 50 | 95 | 10 |
| propyl]- | 16 | 85 | 0 |
| piperidine | 5 | 75 | 0 |
| 1-[3-[p-(1,1- | 500 | 100 | |
| Dimethyl-pentyl)- | 160 | 100 | 100 |
| phenyl]-2-methyl- | 50 | 98 | 92 |
| propyl]-3-methyl- | 16 | 85 | 80 |
| piperdine | 5 | 75 | 20 |
| 4-[3-(p-Tert.amyl- | 500 | 100 | 100 |
| phenyl]-2-methyl- | 160 | 95 | 95 |
| propyl]-2,6- | 50 | 93 | 70 |
| dimethyl- | 16 | 85 | 10 |
| morpholine | 5 | 65 | 0 |
| 1-[3-(4-Tert.amyl- | 500 | 100 | 100 |
| cyclohexyl)-2- | 160 | 95 | 100 |
| methyl-propyl]- | 50 | 85 | 98 |
| piperidine | 16 | 80 | 60 |
| | 5 | 65 | 0 |
| 1-[3-(4-Tert.amyl- | 500 | 100 | |
| cyclohexyl)-2- | 160 | 95 | 98 |
| methyl-2- | 50 | 85 | 93 |
| propenyl]- | 16 | 65 | 65 |
| piperidine | 5 | 60 | 0 |
| 1-[3-[p-(1-Iso- | 500 | 100 | |
| propyl-3-methyl- | 160 | 98 | 100 |
| butyl)-phenyl]-2- | 50 | 80 | 30 |
| methyl-propyl]- | 16 | 75 | 10 |
| piperidine | 5 | 55 | 0 |
| 1-[3-[p-(1-Ethyl- | 500 | | 100 |
| 1-methyl-butyl)- | 160 | 100 | 98 |
| phenyl]-2-methyl- | 50 | 90 | 45 |
| propyl]- | 16 | 40 | 20 |
| piperidine | 5 | 5 | 0 |
| 4-[3-[p-(1-Ethyl- | 500 | | 100 |
| 1-methyl-butyl)- | 160 | 98 | 100 |
| phenyl]-2-methyl- | 50 | 85 | 50 |
| propyl]-2,6- | 16 | 20 | 10 |
| dimethyl- | 5 | 0 | 0 |
| morpholine | | | |
| 4-[3-(4-Biphenyl- | 500 | 100 | |
| yl)-2-methyl- | 160 | 100 | 100 |
| propyl]-2,6- | 50 | 93 | 90 |
| dimethyl- | 16 | 85 | 20 |
| morpholine | 5 | 75 | 10 |
| 1-[3-[p-(α,α- | 500 | | 100 |
| Dimethyl-benzyl)- | 160 | 100 | 100 |
| phenyl]-2-methyl- | 50 | 95 | 100 |
| propyl]- | 16 | 75 | 85 |
| piperidine | 5 | 70 | 65 |
| 1-[3-[p-(α,α- | 500 | 100 | 100 |
| Dimethyl-benzyl)- | 160 | 100 | 100 |
| phenyl]-2-methyl- | 50 | 98 | 100 |
| propyl]-3-methyl- | 16 | 90 | 100 |
| piperidine | 5 | 85 | 97 |
| 4-[3-[p-(α,α- | 500 | 100 | 100 |
| Dimethyl-benzyl)- | 160 | 100 | 100 |
| phenyl]-2-methyl- | 50 | 95 | 100 |
| propyl]-2,6-di- | 16 | 95 | 98 |
| methyl-morpholine | 5 | 90 | 40 |

Table II (*Venturia inaequalis*)

| Test substance | Concentration (in mg/l of spray liquor) | Activity (in %) |
|---|---|---|
| 1-[3-(p-Tert.amyl-phenyl)- | 500 | 100 |
| 2-methyl-propyl]- | 160 | 10 |
| piperidine | 50 | 0 |
| | 16 | 0 |
| | 5 | 0 |
| 1-[3-(p-Tert.amyl-phenyl)- | 500 | 100 |
| 2-methyl-propyl]-3- | 160 | 80 |
| methyl-piperidine | 50 | 50 |
| | 16 | 0 |
| | 5 | 0 |
| 1-[3-[p-(1,1-Dimethyl- | 500 | 100 |

Table II-continued (*Venturia inaequalis*)

| Test substance | Concentration (in mg/l of spray liquor) | Activity (in %) |
|---|---|---|
| pentyl)-phenyl]-2-methyl- | 160 | 95 |
| propyl]-piperidine | 50 | 90 |
| | 16 | 30 |
| | 5 | 10 |
| 4-[3-(p-Tert.amyl-phenyl)- | 500 | 100 |
| 2-methyl-propyl]-2,6- | 160 | 100 |
| dimethyl-morpholine | 50 | 90 |
| | 16 | 50 |
| | 5 | 10 |
| 4-[3-[p-(α,α-Dimethyl- | 500 | 100 |
| benzyl)-phenyl]-2-methyl- | 160 | 100 |
| propyl]-2,6-dimethyl- | 50 | 100 |
| morpholine | 16 | 90 |
| | 5 | 70 |
| 4-[3-[p-(1-Ethyl-1- | 500 | 100 |
| methyl-butyl)-phenyl]-2- | 160 | 100 |
| methyl-propyl]-2,6- | 50 | 95 |
| dimethyl-morpholine | 16 | 50 |
| | 5 | 30 |

The fungicidal agents provided by the present invention can be used according to methods of application which are customary in plant protection. A mixture can be dissolved in suitable solvents, converted into emulsions or dispersions or applied to suitable carriers. In addition to the inert carrier materials, conventional insecticidal, acaricidal, bactericidal and/or other fungicidal compounds can also be added to the mixture so that plant protection agents having a broad spectrum of activity are obtained. For example, the present fungicidal agents can contain O,O-dimethyl-S-(1,2-dicarbethoxyethyl)-dithiophosphate, O,O-diethyl-O-(p-nitrophenyl)-thiophosphate, γ-hexachlorocyclohexane, 2,2-bis-(p-ethylphenyl)-1,1-dichloroethane, p-chlorobenzyl-p-chlorophenyl sulphide, 2,2-bis-(p-chlorophenyl)-1,1,1-trichloroethanol, zinc ethylene-bis-dithiocarbamate, N-trichloromethyl-thiotetrahydrophthalimide, sulfur or the like.

Various inert pulverulent carrier materials, for example, kaolin, bentonite, talc, whiting, magnesium carbonate or kieselguhr can be used to prepare the pulverulent fungicidal agents of this invention. The active ingredients are mixed with these carrier materials, for example, by grinding them together, or the inert carrier materials are impregnated with a solution of the active ingredients and the solvent is then removed by evaporation, heating or by filtration under reduced pressure. Such pulverulent fungicidal agents can be applied to the plants to be protected in the form of dusting agents using a customary dusting apparatus. Such pulverulent fungicidal agents can be rendered easily wettable with water by adding wetting agents and/or dispersing agents so that they can be used in the form of sprays or aqueous suspensions.

In order to prepare emulsifiable concentrates, the active ingredients can, for example, be mixed with an emulsifying agent or dissolved in an inert solvent and mixed with an emulsifier. Ready-to-use emulsions are obtained by diluting such concentrates with water.

Because of their fungistatic and fungicidal activity, the compounds of formula I are also suitable for combatting infections which are caused by fungi and yeasts; for example, those of the genera Candida, Trichophytes or Histoplasma. The compounds of formula I are particularly active against Candida species, such as, *Candida*

*albicans* and are particularly suitable for the local therapy of superficial infections of the skin and of the mucous membranes, in particular of the genital tract, for example, vaginitis, especially that caused by Candida. The chosen form of administration is local, for example, the compounds are used in the form of ointments, miniature suppositories, suppositories, ovules or other suitable forms.

The pharmaceutical preparations can be prepared in a known manner by mixing the compounds of formula I with customary organic or inorganic inert excipients and/or auxiliaries, such as, water, gelatin, lactose, starch, magnesium stearate, talc, vegetable oils, polyalkylene glycols, petroleum jelly, preservatives, stabilizers, wetting agents, emulsifiers, salts for modifying the osmotic pressure or buffers.

The oral dosage administered will depend on individual requirements, but a daily administration of 1-2 tablets containing 100 mg. of active ingredient for a few days can be a preferred dosage. The ointments appropriately contain 0.3%-5%, preferably 0.5%-2% and particularly preferably 0.5%-1%, of active ingredient. The experimental reports and the results given in Table III hereinafter also provide appropriate information appertaining to the dosage of the active ingredients.

(a) Test: Candida albicans in vitro

Method: A standardised suspension of the yeast form of Canadida albicans strain H 29 (ca 300 cells/5 ml, fifty times the lowest number of germs necessary for starting the culture) is poured into a Rowley and Huber agar nutrient medium, liquefied and cooled to 50° C., simultaneously with suitable formulation solutions. The formulations are dissolved in water or polyethylene glycol (Carbowax 400). Formulations which are soluble neither in water nor in polyethylene glycol are finely suspended. The final concentrations of the formulations in the nutrient medium are 100, 10 and 1 mcg/ml and the final concentration of polyethylene glycol is 5%. Incubation is carried out at 37° C. for 7 days.

Evaluation: Assessment of the fungal growth with the naked eye.

Results: The minimum formulation concentration, in mcg/ml, which completely prevents growth of the fungus is given (MIC). The results of some test are summarized in Table III hereinafter.

(b) Test: Trichophyton mentagrophytes in vitro

Method: A standardised suspension of the yeast form of conidia (spores) of Trichophyton mentagrophytes strain 109 (ca fifty times the lowest number of germs necessary for starting the culture) is poured into Rowley and Huber agar nutrient medium, liquefied and cooled to 50° C., simultaneously with suitable formulation solutions. The formulations are dissolved in water or polyethylene glycol (Carbowax 400). Formulations which are soluble neither in water nor in polyethylene glycol are finely suspended. The final concentrations of the formulations in the nutrient medium are 100, 10, 1, 0.1 and 0.01 mcg/ml. The final concentration of polyethylene glycol is 5%. Incubation is carried out at 37° C. for 7 days.

Evaluation: Assessment of the fungal growth with the naked eye.

Results: The minimum formulation concentration, in mcg/ml, which completely prevents growth of the fungus is given (MIC). The results of some tests are summarized in Table III hereinafter.

(c) Test: Histoplasma capsulatum in vitro

Method: A standardised suspension of the yeast form of Histoplasma capsulatum strain Hist 2 (ca fifty times the lowest number of germs necessary for starting the culture) is poured into Rowley and Huber agar nutrient medium, liquefied and cooled to 50° C., simultaneously with suitable formulation solutions. The formulations are dissolved in water or polyethylene glycol (Carbowax 400). Formulations which are soluble neither in water nor in polyethylene glycol are finely suspended. The final concentration of the formulations in the nutrient medium is 100, 10, 1, 0.1 and 0.01 mcg/ml. The final concentration of polyethylene glycol is 5%. Incubation is carried out at 28° C. for 12 days.

Evaluation: Assessment of the fungal growth with the naked eye.

Results: The minimum formulation concentration, in mcg/ml, which completely prevents growth of the fungus is given (MIC). The results of some tests are summarized in Table III hereinafter.

Table III

| | MIC (μg/ml) | | |
|---|---|---|---|
| Test substance | *Candida albicans* | *Trichophyton mentagr.* | *Histoplasma capsulatum* |
| 1-[3-(p-Isobutyl-phenyl)-2-methyl-propyl]-piperidine | 10 | 1 | 1 |
| 1-[3-(p-Tert.amyl-phenyl)-2-methyl-propyl]-piperidine | 10 | 0.01 | 0.01 |
| 1-[3-[p-(α,α-Dimethyl-benzyl)-phenyl]-2-methyl-propyl]-piperidine | 10 | 1 | 0.01 |
| 4-[3-[p-(α,α-Dimethyl-benzyl)-phenyl]-2-methyl-propyl]-2,6-dimethyl-morpholine | 0.01 | 1 | 0.01 |
| 4-[3-(p-Tert.amyl-phenyl)-2-methyl-propyl]-2,6-dimethyl-morpholine | 1 | 0.1 | 0.1 |
| 1-[3-[p-(1,1-Dimethyl-pentyl)-phenyl]-2-methyl-propyl]-piperidine | 1 | 0.1 | 0.01 |
| 1-[3-[p-(1,1-Dimethyl-pentyl)-phenyl]-2-methyl-propyl]-3-methyl-piperidine | 1 | 1 | 0.01 |
| 1-[3-[p-(α,α-Dimethyl-benzyl)-phenyl]-2-methyl-propyl]-3-methyl-piperidine | 1 | 1 | 0.01 |
| 1-[3-[p-(1,2-Dimethyl-propyl)-phenyl]-2-methyl-propyl]-piperidine | 10 | 1 | 0.1 |

MIC=minimum inhibitory concentration. The values given are in most cases maximum values, that is, the minimum inhibitory concentration can be lower. The compounds of formula I also show the antimycotic activity described earlier in "in vivo" experiments.

The following Examples further illustrate the invention. All temperatures are stated in degrees Centigrade, unless otherwise mentioned.

I. PREPARATION OF THE SPRAYABLE POWDERS USED IN THE BIOLOGICAL EXPERIMENTS AND OF OTHER FORMULATIONS:

1. Sprayable powder appropriate for all compounds of formula I

Example 1

| | w/w %* |
|---|---|
| Active ingredient | 25.0 |
| Finely divided hydrated silicic acid | 25.0 |
| Methylhydroxyethylcellulose | 1.0 |
| Sodium oleate | 2.0 |
| Nonylphenol-ethylene oxide adduct | 3.0 |
| Sodium salt of dinaphthyl methane sulfonic acid | 10.0 |
| Kaolin B 24 | 34.0 |
| | 100.0 |

*Weight percent

Solid active ingredients are mixed with the silicic acid or liquid active ingredients are taken up on the silicic acid. The customary additives are added and the mixture is homogeneously mixed in a suitable apparatus. The resulting powder is then finely milled in a suitable grinding apparatus, for example, a pinned disc mill, hammer mill, ball mill, air-jet mill, or the like, and thereafter again mixed.

2. Seed disinfectant appropriate for all compounds of formula I

Example 2

| | % w/w |
|---|---|
| Active ingredient | 20.0 |
| Calcium silicate | 20.0 |
| Red iron oxide pigment | 8.0 |
| Roter xanthene colourant (Colour Index: Solvent Red 49) | 0.5 |
| Starch hydrolysate-powder (dextrin) | 2.0 |
| Sulphite pulp spent liquor-powder | 3.2 |
| Sodium butylnaphthylsulphonate | 2.0 |
| Kaolin b 24 | 44.3 |
| | 100.0 |

The solid active ingredient is mixed with calcium silicate or liquid active ingredient is taken up on calcium silicate. The customary additives are added and the mixture is mixed and milled (see Example 1). The resulting red powder can be used tel quel as a dry disinfectant for seeds or can be diluted with water to form a liquid disinfectant for seeds.

3. Emulsifiable concentrate appropriate for oily compounds of formula I

Example 3

| | | g/l |
|---|---|---|
| Active ingredient [for example, 1-[3-(p-tert.-amyl-phenyl)-2-methyl-propyl]-piperidine] | | 500 |
| Castor oil-ethyleneoxide-adduct | | 100 |
| Calcium salt of dodecylbenzenesulfonic acid | | 50 |
| Aromatic solvent (mixture of $C_{10}$-alkyl-benzenes) | ad | 1000 ml. |

The active substance is dissolved in a portion of the aromatic solvent, the customary additives are added and dissolved, and the mixture is made up to volume with the remainder of the solvent. The resulting product is added to water in order to prepare a ready-for-use spray liquor, whereby there is obtained an emulsion (oil/water) which is stable for hours.

4. Water-soluble concentrate appropriate for water-soluble compounds of formula I Example 4

| | | g/l |
|---|---|---|
| Active ingredient [for example, 1-[3-(p-tert.-amyl-phenyl)-2-methyl-propyl]-piperidine 1-oxide] | | 250 |
| Isopropanol | | 300 |
| Water, deionized | ad | 1000 ml. |

The active ingredient is dissolved in isopropanol and made up to volume with water. This concentrate, which is stable to temperatures which are as low as −5° C., can be appropriately diluted with water in order to prepare a ready-for-use spray liquor, whereby there is obtained a solution in the form of a molecular dispersion.

Example 5

| | | g/l |
|---|---|---|
| Active ingredient [for example, 1-[3-(p-tert.-amyl-phenyl)-2-methyl-propyl]-piperidine 1-oxide] | | 250 |
| Dispersion of a copolymeric vinyl acetate/ethylene, solid body weight about 50% | | 50 |
| Water, deionized | ad | 1000 m. |

The active ingredient is dissolved in a portion of the water, the copolymer dispersion is then stirred in and the mixture is made up to volume with the remainder of the water. The resulting homogeneous dispersion can be diluted with the appropriate amount of water to form a ready-for-use spray liquor. The copolymer dispersion confers to the liquor an improved adhesion to the aerial parts of plants.

5. Formulations appropriate for compounds of formula I which contain a protonisable nitrogen atom This type of formulation contains salts and molecular and addition products of the compounds provided by the invention; for example,

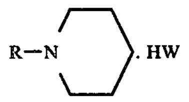

wherein HW is an acid or an acid mixture which preferably has a pK value of less than 5.0.

In this connection, there preferably come into consideration organic acids which form salts which are soluble in water, in mixtures of water and water-soluble solvents and in non-polar solvents.

The salts are preferably prepared in situ during the formulation of the active ingredients by adding a stoichiometric amount of HW in the presence of water and/or organic solvents or solid carrier materials at usual temperatures.

Example 6

| | | g/l |
|---|---|---|
| Active ingredient [for example, 4-[3-(p-tert.-amyl-phenyl)-2-methyl-propyl]-2,6-dimethyl-morpholine] | | 250 |
| Acetic acid (100%) (pK: 4.75) | | 35 |
| Lactic acid (90%) (pK: 3.08) | | 25 |
| Isopropanol | | 300 |
| Water, deionized | ad | 1000 ml. |

The active ingredient is dissolved in isopropanol. The lactic acid and the acetic acid are added while stirring. A relatively strong warming-up takes place. The mixture is made up to volume with water. The resulting clear, practically colorless solution (a water-soluble concentrate) can be diluted with water to give a ready-for-use spray liquor.

Example 7

| | | g/l |
|---|---|---|
| Active ingredient [for example, 1-[3-(p-tert.-amyl-phenyl)-2-methyl-propyl]-piperidine] | | 250 |
| Methanesulfonic acid | | 84 |
| Water, deionized | ad | 1000 ml. |

The methanesulphonic acid is added dropwise while stirring to a portion of the water, a very strong warming-up taking place. After cooling to room temperature, the mixture is made up to volume with water. The resulting clear, slightly yellowish solution (a water-soluble concentrate) can be diluted with water to give a ready-for-use spray liquor.

Example 8

| | | g/l |
|---|---|---|
| Active ingredient [for example, 1-[3-(p-tert.-amyl-phenyl)-2-methyl-propyl]-piperidine] | | 250 |
| Bis-(2-ethylhexyl)-phosphoric acid | | 140 |
| Emulsifier | | 100* |
| Aromatic solvent (mixture of $C_{10}$-alkylbenzenes) | ad | 1000 ml. |

*Mixture of nonylphenol-ethyleneoxide adducts, dodecylbenzenesulfonic acid calcium salt and solvent.

The active ingredient is dissolved in a portion of the aromatic solvent and then the bis-(2-ethylhexyl)-phosphoric acid is stirred in dropwise, a moderate warming-up taking place. The still warm mixture is treated with the emulsifier, the resulting mixture is cooled to room temperature and made up to volume with the aromatic solvent. In order to prepare a ready-for-use spray liquor, the product obtained (an emulsifiable concentrate) is stirred into water, whereby there is obtained an emulsion (oil/water).

Example 9

| | | g/l |
|---|---|---|
| Active ingredient [for example, 1-[3-(p-tert.-amyl-phenyl)-2-methyl-propyl]-piperidine] | | 250 |
| Phosphoric acid monoester and diester of nonyl-phenolpolyglycol ether | | 386 |
| Dimethylformamide | | 200 |
| 1,1,1-Trichloroethane | ad | 1000 ml. |

The active ingredient is dissolved in the dimethylformamide and then the phosphoric acid ester is stirred in dropwise, an appreciable warming-up taking place. After cooling, the mixture is made up to volume with 1,1,1-trichloroethane. In order to prepare a finished spray liquor, the product obtained (an emulsifiable concentrate) is stirred into water, whereby there is obtained an emulsion (oil/water) which is stable for hours.

A typical feature of this formulation is the presence of a tensioactive acid which makes the addition of an emulsifier superfluous.

Example 10

| | w/w % |
|---|---|
| Active ingredient [for example, 1-[3-(p-tert.-amyl-phenyl)-2-methyl-propyl]-piperidine] | 25.0 |
| Sulfamic acid | 9.0 |
| Finely divided hydrated silicic acid | 25.0 |
| Mixture of 85% sodium dioctylsulfosuccinate and 15% sodium benzoate | 1.0 |
| Diammonium hydrogen phosphate | 40.0 |

The active ingredient is mixed with the silicic acid to give a dry powder. The remaining additives are then admixed and the resulting mixture is finely milled in a suitable grinding apparatus (see Example 1). In order to prepare a finished spray liquor, the product obtained (a water-soluble powder) is diluted with water.

II. PREPARATION OF THE COMPOUNDS OF FORMULA I:

Example 11

Preparation of 1-[3-(p-tert.-amyl-phenyl)-2-methyl-propyl]-piperidine 21.8 G. of 3-(p-tert.-amyl-phenyl)-2-methyl-propionaldehyde and 11.3 g. of piperidine are heated at reflux in 15 ml. of toluene in a water-separator under nitrogen gasification until the water-cleavage has been completed (6 hours). Subsequently, there are added dropwise at room temperature with stirring 6.9 g. of formic acid, the temperature rising to 36°–40° C. Then, the mixture is heated to 75° C. for 2 hours, 50 Ml. of 2 N hydrochloric acid are added to the cooled solution. The toluene solution is separated. The aqueous-hydrochloric acid solution is made alkaline with 40 ml. of 6 N sodium hydroxide and the product is extracted with ether. The combined ether extracts are washed with water, dried over sodium sulfate and evaporated. By distillation, there is obtained pure 1-[3-(p-tert.-amyl-phenyl)-2-methyl-propyl]-piperidine having a boiling point of 160° C./0.15 Torr.

Example 12

Preparation of 4-[3-(p-tert.-amyl-phenyl)-2-methyl-propyl]-2,6-dimethylmorpholine 230 G. of 3-(p-tert.-amyl-phenyl)-2-methyl-propionaldehyde and 137 g. of 2,6-dimethylmorpholine are heated at reflux in 1000 ml. of toluene for 16 hours in a water-separator under nitrogen gasification until the water-cleavage has been completed. 17.5 G. of 5% palladium/carbon are added at room temperature under nitrogen gasification and the mixture is subsequently hydrogenated until the hydrogen uptake has been completed. Then, the catalyst is removed by filtration and the toluene is evaporated in vacuo. By distillation of the residue, there is obtained pure 4-[3-(p-tert.-amylphenyl)-2-methyl-propyl]-2,6-dimethylmorpholine having a boiling point of 134° C./0.036 Torr.

In an analogous manner, from 3-(p-tert.-amyl-phenyl)-2-methyl-propionaldehyde and 3-methyl-piperidine there is obtained, after hydrogenation, 1-[3-(p-tert.-amyl-phenyl)-2-methyl-propyl]-3-methylpiperidine having a boiling point of 164° C./0.15 Torr, from 3-(p-neopentyl-phenyl)-2-methyl-propionaldehyde and 2,6-dimethyl-morpholine there is obtained, after hydrogenation, 4-[3-(p-neopentyl-phenyl)-2-methyl-propyl]-2,6-dimethyl-morpholine of boiling point 130° C./0.055 Torr, from 3-(p-neopentyl-phenyl)-2-methyl-propionaldehyde and piperidine there is obtained, after hydrogenation, 1-[3-(p-neopentyl-phenyl)-2-methyl-propyl]-piperidine of boiling point 104° C./0.09 Torr, from 3-(p-neopentyl-phenyl)-2-methyl-propionaldehyde and 3-methyl-piperidine there is obtained, after hydrogenation, 1-[3-(p-neopentyl-phenyl)-2-methyl-propyl]-3-methyl-piperidine of boiling point 119° C./0.09 Torr, from 3-(p-isobutyl-phenyl)-2-methyl-propionaldehyde and piperidine there is obtained, after hydrogenation, 1-[3-(p-isobutyl-phenyl)-2-methyl-propyl]-piperidine of boiling point 105°-110° C./0.028 Torr, from 3-(p-isobutyl-phenyl)-2-methyl-propionaldehyde and 2,6-dimethyl-morpholine there is obtained, after hydrogenation, 4-[3-(p-isobutyl-phenyl)-2-methyl-propyl]-2,6-dimethyl-morpholine of boiling point 92°-95° C./0.024 Torr, from 3-[p-(1,1-dimethyl-pentyl)-phenyl]-2-methyl-propionaldehyde and piperidine there is obtained, after hydrogenation, 1-[3-[p-(1,1-dimethyl-pentyl)-phenyl]-2-methyl-propyl]-piperidine of boiling point 135°-136° C./0.035 Torr, from 3-[p-(1,1-dimethyl-pentyl)-phenyl]-2-methyl-propionaldehyde and 3-methyl-piperidine there is obtained, after hydrogenation, 1-[3-[p-(1,1-dimethyl-pentyl)-phenyl]-2-methyl-propyl]-3-methyl-piperidine of boiling point 132°-133° C./0.035 Torr, from 3-[p-(1,1-diethyl-propyl)-phenyl]-2-methyl-propionaldehyde and piperidine there is obtained, after hydrogenation, 1-[3-]p-(1,1-diethyl-propyl)-phenyl]-2-methyl-propyl]-piperidine of boiling point 158° C./0.07 Torr, from 3-[p-(1,1-diethyl-propyl)-phenyl]-2-methyl-propionaldehyde and 3-methyl-piperidine there is obtained, after hydrogenation, 1-[3-[p-(1,1-diethyl-propyl)-phenyl]-2-methyl-propyl]-3-methyl-piperidine of boiling point 132° C./0.05 Torr, from 3-(p-biphenylyl)-2-methyl-propionaldehyde and piperidine there is obtained, after hydrogenation, 1-[3-(p-biphenylyl)-2-methyl-propyl]-piperidine of boiling point 149°-151° C./0.02 Torr, from 3-(p-biphenylyl)-2-methyl-propionaldehyde and 3-methyl-piperidine there is obtained, after hydrogenation, 1-[3-(p-biphenylyl)-2-methyl-propyl]-3-piperidine of boiling point 154°-155° C./0.02 Torr, from 3-(p-tert.butyl-phenyl)-2-ethyl-propionaldehyde and piperidine there is obtained, after hydrogenation, 1-[3-(p-tert.butyl-phenyl)-2-ethyl-propyl]-piperidine of boiling point 107°-110° C./0.02 Torr, from 3-(p-tert.butyl-phenyl)-2-ethyl-propionaldehyde and 3-methyl-piperidine there is obtained, after hydrogenation, 1-[3-(p-tert.butyl-phenyl)-2-ethyl-propyl]-3-methyl-piperidine of boiling point 119°-122° C./0.022 Torr, from 3-(p-tert.butyl-phenyl)-2-isopropyl-propionaldehyde and piperidine there is obtained, after hydrogenation, 1-[2-(p-tert.butyl-benzyl)-3-methyl-butyl]-piperidine of boiling point 107°-108° C./0.02 Torr, from 3-(p-tert.butyl-phenyl)-2-isopropyl-propionaldehyde and 3-methyl-piperidine there is obtained, after hydrogenation, 1-[2-(p-tert.butyl-benzyl)-3-methyl-butyl]-3-methyl-piperidine of boiling point 110°-115° C./0.02 Torr, from 2-(p-tert.butyl-benzyl)-decanal and piperidine there is obtained, after hydrogenation, 1-[2-(p-tert.butyl-benzyl)-decyl]-piperidine of boiling point 150°-153° C./0.023 Torr, from 2-(p-tert.butyl-benzyl)-decanal and 3-methyl-piperidine there is obtained, after hydrogenation, 1-[2-(p-tert.butyl-benzyl)-decyl]-3-methyl-piperidine of boiling point 147°-152° C./0.023 Torr, from 3-(p-tert.amyl-phenyl)-2-methyl-propionaldehyde and 3,5-dimethyl-piperidine there is obtained, after hydrogenation, 1-[3-(p-tert.amyl-phenyl)-2-methyl-propyl]-3,5-dimethyl-piperidine of boiling point 135° C./0.05 Torr, from 3-[p-(1-ethyl-1-methyl-butyl)-phenyl]-2-methyl-propionaldehyde and piperidine there is obtained, after hydrogenation, 1-[3-[p-(1-ethyl-1-methyl-butyl)-phenyl]-2-methyl-propyl]-piperidine of boiling point 137° C./0.05 Torr, from 3-[p-(1-ethyl-1-methyl-butyl)-phenyl]-2-methyl-propionaldehyde and 2,6-dimethyl-morpholine there is obtained, after hydrogenation, 4-[3-[p-(1-ethyl-1-methyl-butyl)-phenyl]-2-methyl-propyl]-2,6-dimethyl-morpholine of boiling point 143° C./0.05 Torr, from 3-[p-(1,2-dimethyl-propyl)-phenyl]-2-methyl-propionaldehyde and piperidine there is obtained, after hydrogenation, 1-[3-[p-(1,2-dimethyl-propyl)-phenyl]-2-methyl-propyl]-piperidine of boiling point 106° C./0.04 Torr, from 3-[p-(1,2-dimethyl-propyl)-phenyl]-2-methyl-propionaldehyde and 2,6-dimethyl-morpholine there is obtained, after hydrogenation, 4-[3-[p-(1,2-dimethyl-propyl)-phenyl]-2-methyl-propyl]-2,6-dimethyl-morpholine of boiling point 110° C./0.04 Torr, from 3-[p-(1-isopropyl-3-methyl-butyl)-phenyl]-2-methyl-propionaldehyde and piperidine there is obtained, after hydrogenation, 1-[3-[p-(1-isopropyl-3-methyl-butyl)-phenyl]-2-methyl-propyl]-piperidine of boiling point 117° C./0.08 Torr, from 3-[p-(1-isopropyl-3-methyl-butyl)-phenyl]-2-methyl-propionaldehyde and 2,6-dimethyl-morpholine there is obtained, after hydrogenation, 4-[3-[p-(1-isopropyl-3-methyl-butyl)-phenyl]-2-methyl-propyl]-2,6-dimethyl-morpholine of boiling point 120° C./0.08 Torr, from 3-[p-(α,α-dimethyl-benzyl)-phenyl]-2-methyl-propionaldehyde and piperidine there is obtained, after hydrogenation, 1-[3-[p-(α,α-dimethyl-benzyl)-phenyl]-2-methyl-propyl]-piperidine of boiling point 162° C./0.03 Torr, from 3-[p-(α,α-dimethyl-benzyl)-phenyl]-2-methyl-propionaldehyde and 3-methyl-piperidine there is obtained, after hydrogenation, 1-[3-[p-(α,α-dimethyl-benzyl)-phenyl]-2-methyl-propyl]-3-methyl-piperidine of boiling point 167° C./0.04 Torr, from 3-[p-(α,α-dimethyl-benzyl)-phenyl]-2-methyl-propionaldehyde and 2,6-dimethyl-morpholine there is obtained, after hydrogenation, 4-[3-[p-(α,α-dimethyl-benzyl)-phenyl]-2-methyl-propyl]-2,6-dimethyl-morpholine of boiling point 162° C./0.04 Torr, from 3-[p-(2-cyclohexyl-1,1-dimethyl-ethyl)-phenyl]-2-methyl-propionaldehyde and piperidine there is obtained, after hydrogenation, 1-[3-[p-(2-cyclohexyl-1,1-dimethyl-ethyl)-phenyl]-2-methyl-propyl]-piperidine of boiling point 175° C./0.035 Torr,
from 3-[p-(2-cyclohexyl-1,1-dimethyl-ethyl)-phenyl]-2-methyl-propionaldehyde and 2,6-dimethyl-morpholine there is obtained, after hydrogenation, 4-[3-[p-(2-cyclohexyl-1,1-dimethyl-ethyl)-phenyl]-2-methyl-propyl]-2,6-dimethyl-morpholine of boiling point 165° C./0.035 Torr,
from 3-[p-(1-propyl-1-methyl-pentyl)-phenyl]-2-methyl-propionaldehyde and piperidine there is obtained, after hydrogenation, 1-[3-[p-(1-propyl-1-methyl-pentyl)-phenyl]-2-methyl-propyl]-piperidine of boiling point 137° C./0.035 Torr,
from 3-[p-(1-propyl-1-methyl-pentyl)-phenyl]-2-methyl-propionaldehyde and 2,6-dimethyl-morpholine there is obtained, after hydrogenation, 4-[3-[p-(1-propyl-1-methyl-pentyl)-phenyl]-2-methyl-propyl]-2,6-dimethyl-morpholine of boiling point 158° C./0.04 Torr,
from 3-[p-(1-propyl-1-methyl-pentyl)-phenyl]-2-methyl-propionaldehyde and 3,5-dimethyl-piperidine there is obtained, after hydrogenation, 1-[3-[p-(1-propyl-1-methyl-pentyl)-phenyl]-2-methyl-propyl]-3,5-dimethyl-piperidine of boiling point 144° C./0.44 Torr,
from 3-[p-(1-cyclohexyl-1-methyl)-phenyl]-2-methyl-propionaldehyde and piperidine there is obtained, after hydrogenation, 1-[3-[p-(1-cyclohexyl-1-methyl)-phenyl]-2-methyl-propyl]-piperidine of boiling point 140° C./0.04 Torr,
from 3-[p-(1-cyclohexyl-1-methyl)-phenyl]-2-methyl-propionaldehyde and 3,5-dimethyl-piperidine there is obtained, after hydrogenation, 1-[3-[p-(1-cyclohexyl-1-methyl)-phenyl]-2-methyl-propyl]-3,5-dimethyl-piperidine of boiling point 130° C./0.04 Torr,
from 3-[p-(1-cyclohexyl-1-methyl)-phenyl]-2-methyl-propionaldehyde and 2,6-dimethyl-morpholine there is obtained, after hydrogenation, 4-[3-[p-(1-cyclohexyl-1-methyl)-phenyl]-2-methyl-propyl]-2,6-dimethyl-morpholine of boiling point 160° C./0.07 Torr,
from 3-(4-biphenylyl)-2-methyl-propionaldehyde and 3-ethyl-piperidine there is obtained, after hydrogenation, 1-[3-(4-biphenylyl)-2-methyl-propyl]-3-ethyl-piperidine of boiling point 174° C./0.04 Torr,
from 3-(4-biphenylyl)-2-methyl-propionaldehyde and 2,6-dimethyl-morpholine there is obtained, after hydrogenation, 4-[3-(4-biphenylyl)-2-methyl-propyl]-2,6-dimethyl-morpholine of boiling point 160° C./0.05 Torr,
from 3-(p-benzyl-phenyl)-2-methyl-propionaldehyde and piperidine there is obtained, after hydrogenation, 1-[3-(4-benzyl-phenyl)-2-methyl-propyl]-piperidine of boiling point 147° C./0.04 Torr, and
from 3-(p-benzyl-phenyl)-2-methyl-propionaldehyde and 2,6-dimethyl-morpholine there is obtained, after hydrogenation, 4-[3-(4-benzyl-phenyl)-2-methyl-propyl]-2,6-dimethyl-morpholine of boiling point 155° C./0.04 Torr.

Example 13

Preparation of 1-[3-(p-tert.-amyl-phenyl)-2,3-dimethyl-2-propenyl]-3,5-dimethylpiperidine 62 G. of 3-(p-tert.-amyl-phenyl)-2,3-dimethyl-allyl bromide in 150 ml. of ether are added dropwise to a solution of 45.2 g. of 3,5-dimethylpiperidine in 200 ml. of absolute ether and the mixture is heated at reflux for 16 hours. The 3,5-dimethylpiperidine hydrobromide is removed by filtration and back-washed with ether. The ether solution is extracted with 2 N hydrochloric acid and made alkaline with 50% sodium hydroxide. The alkaline-aqueous solution is again extracted with ether, washed with water, dried over sodium sulfate and evaporated. By distillation, there is obtained pure 1-[3-(p-tert.-amylphenyl)-2,3-dimethyl-2-propenyl]-3,5-dimethylpiperidine having a boiling point of 155° C./0.04 Torr.

In an analogous manner,
from 3-(p-tert.amyl-phenyl)-2,3-dimethyl-allyl bromide and 2,6-dimethyl-morpholine there is obtained 4-[3-(p-tert.amyl-phenyl)-2,3-dimethyl-2-propenyl]-2,6-dimethyl-morpholine of boiling point 152° C./0.05 Torr,
from 3-(p-cyclohexyl-phenyl)-2-methyl-allyl bromide and piperidine there is obtained 1-[3-(p-cyclohexyl-phenyl)-2-methyl-2-propenyl]-piperidine of boiling point 165° C./0.01 Torr,
from 3-[p-(α,α-dimethyl-benzyl)-phenyl]-2,3-dimethyl-allyl bromide and 3,5-dimethyl-piperidine there is obtained 1-[3-[p-(α,α-dimethyl-benzyl)-phenyl]-2,3-dimethyl-2-propenyl]-3,5-dimethyl-piperidine of boiling point 176°-178° C./0.04 Torr,
from 3-(4-tert.amyl-cyclohexyl)-2-methyl-allyl bromide and piperidine there is obtained 1-[3-(4-tert.amyl-cyclohexyl)-2-methyl-2-propenyl]-piperidine of boiling point 110°-118° C./0.023 Torr, and
from 3-(4-tert.amyl-cyclohexyl)-2-methyl-allyl bromide and 2,6-dimethyl-morpholine there is obtained 4-[3-(4-tert.amyl-cyclohexyl)-2-methyl-2-propenyl]-2,6-dimethyl-morpholine of boiling point 120°-127° C./0.029 Torr.

Example 14

Preparation of 4-[3-(p-tert.-amyl-phenyl)-2,3-dimethyl-propyl]-2,6-dimethylmorpholine 1.8 Ml. of 32% hydrochloric acid and subsequently 1.5 g. of 5% palladium/carbon are added to a solution of 4.5 g. of 4-[3-(p-tert.-amyl-phenyl)-2,3-dimethyl-2-propenyl]2,6-dimethylmorpholine in 125 ml. of alcohol and the mixture is hydrogenated. After completion of the hydrogen uptake, the catalyst is removed by filtration, the filtrate is treated with 200 ml. of 10% sodium hydroxide and then extracted with ether. The combined ether extracts are washed neutral with water, dried and evaporated. By distillation, there is obtained pure 4-[3-(p-tert.-amyl-phenyl)-2,3-dimethyl-propyl]-2,6-dimethylmorpholine having a boiling point of 145° C./0.05 Torr.

In an analogous manner, from 1-[3-[p-(α,α-dimethyl-benzyl)-phenyl]-2,3-dimethyl-2-propenyl]-3,5-dimethyl-piperidine there is obtained, after hydrogenation, 1-[3-[p-(α,α-dimethyl-benzyl)-phenyl]-2,3-dimethyl-propyl]-3,5-dimethyl-piperidine of boiling point 178° C./0.04 Torr.

Example 15

Preparation of 1-[3-(4-tert.-amyl-cyclohexyl)-2-methyl-propyl]-piperidine

7 G. of platinum dioxide and 7 g. of active carbon are suspended in 500 ml. of glacial acetic acid and prehydrogenated. Subsequently, there is added a solution of 37.4 g. of 1-[3-(p-tert.-amyl-phenyl)-2-methyl-propyl]- piperidine in 1000 ml. of glacial acetic acid and 67 ml. of perchloric acid and the mixture is hydrogenated at 25° C. The hydrogenation solution is filtered to remove the catalyst and the filtrate is treated with 110 g. of potassium acetate dissolved in 100 ml. of water. The precipiated potassium perchlorate is removed by filtration and the filtrate is evaporated on a rotary evaporator. The crystalline residue is made alkaline with 2 N sodium hydroxide, the free base is extracted with 500 ml. of ether, washed neutral with water, dried over sodium sulfate and evaporated. By distillation, there is obtained pure 1-[3-(4-tert.-amylcyclohexyl)-2-methyl-propyl]-piperidine, having a boiling point of 128°-132° C./0.04 Torr.

In an analogous manner, from 1-[3-[p-(α,α-dimethyl-benzyl)-phenyl]-2-methyl-propyl]-piperidine there is obtained 1-[3-[4-(1-cyclohexyl-1-methyl-ethyl)-cyclohexyl]-2-methyl-propyl]-piperidine of boiling point 156° C./0.04 Torr, and from 4-[3-[p-(α,α-dimethyl-benzyl)-phenyl]-2-methyl-propyl]-2,6-dimethyl-morpholine there is obtained 4-[3-[4-(1-cyclohexyl-1-methyl-ethyl)-cyclohexyl]-2-methyl-propyl]-2,6-dimethyl-morpholine of boiling point ca 145° C./0.03 Torr (bulb-tube).

Example 16

Preparation of 1-[3-(p-tert.-amyl-phenyl)-2-methyl-propyl]-piperidine 1-oxide 7.2 g of 30% hydrogen peroxide are added dropwise at 40° C. to a solution of 5.8 g of 1-[3-(p-tert.amyl-phenyl)-2-methyl-propyl]-piperidine in 20 ml of isopropanol and this addition is repeated after 24 hours. After stirring at 40° C. for 60 hours, the mixture is cooled and the excess hydrogen peroxide is decomposed by addition of platinum sponge. The solution is filtered, the filtrate is evaporated, the residue is taken up in 50 ml of water and extracted with hexane. The aqueous solution is subsequently evaporated and the residue is dried in a high vacuum. There is obtained pure 1-[3-(p-tert.amyl-phenyl)-2-methyl-propyl]-piperidine-1-oxide; $n_D^{20}=1.5180$.

The following Examples illustrate the preparation of the starting materials:

Example 17

Preparation of 3-(p-tert.-amyl-phenyl)-2-methyl-acrolein 162.2 g of p-tert.amyl-benzaldehyde are added under nitrogen gasification to a solution of 1.56 g of potassium hydroxide in 113 ml of methanol and 48.8 g of propionaldehyde are subsequently added dropwise at 40° C. over a period of 6 hours. The mixture is subsequently stirred at 40° C. for an additional hour, 2 ml of acetic acid are added and the mixture is concentrated on a rotary evaporator. The oily suspension is taken up in ether, washed neutral with water, dried and evaporated. By distillation there is obtained pure 3-(p-tert.amyl-phenyl)-2-methyl-acrolein of boiling point 117°-120° C./0.035 Torr.

In an analogous manner, from p-(1-ethyl-1-methyl-butyl)-benzaldehyde and propionaldehyde there is obtained 3-[p-(1-ethyl-1-methyl-butyl)-phenyl]-2-methyl-acrolein of boiling point 107°-112° C./0.05 Torr, from p-(1,2-dimethyl-propyl)-benzaldehyde and propionaldehyde there is obtained 3-[p-(1,2-dimethyl-propyl)-phenyl]-2-methyl-acrolein of boiling point 110° C./0.05 Torr, from p-(1-isopropyl-3-methyl-butyl)-benzaldehyde and propionaldehyde there is obtained 3-[p-(1-isopropyl-3-methyl-butyl)-phenyl]-2-methyl-acrolein of boiling point ca 105°-110° C./0.05 Torr (bulb-tube), from p-(α,α-dimethyl-benzyl)-benzaldehyde and propionaldehyde there is obtained 3-[p-(α,α-dimethyl-benzyl)-phenyl]-2-methyl-acrolein of boiling point 167°-177° C./0.05 Torr, from p-(2-cyclohexyl-1,1-dimethyl-ethyl)-benzaldehyde and propionaldehyde there is obtained 3-[p-(2-cyclohexyl-1,1-dimethyl-ethyl)-phenyl]-2-methyl-acrolein of boiling point 143°-148° C./0.04 Torr, from p-(1-propyl-1-methyl-pentyl)-benzaldehyde and propionaldehyde there is obtained 3-[p-(1-propyl-1-methyl-pentyl)-phenyl]-2-methyl-acrolein of boiling point 136° C./0.05 Torr, from p-(1-cyclohexyl-1-methyl)-benzaldehyde and propionaldehyde there is obtained 3-[p-(1-cyclohexyl-1-methyl)-phenyl]-2-methyl-acrolein of boiling point 140°-145° C./0.05 Torr, from p-benzyl-benzaldehyde and propionaldehyde there is obtained 3-(p-benzyl-phenyl)-2-methyl-acrolein of boiling point 155° C./0.04 Torr, from p-tert.butyl-benzaldehyde and decanal there is obtained 3-(p-tert.butyl-phenyl)-2-octyl-acrolein of boiling point 141°-154° C./0.02 Torr, and from p-phenyl-benzaldehyde and propionaldehyde there is obtained 3-(p-biphenylyl)-2-methyl-acrolein of melting point 95° C.

Example 18

Preparation of 3-(p-tert.-amyl-phenyl)-2-methyl-allyl alcohol 432.62 g of 3-(p-tert.amyl -phenyl)-2-methyl-acrolein are dissolved in 2500 ml of methanol and treated portionwise while cooling with ice with 38 g of sodium borohydride. Subsequently, the mixture is stirred at room temperature for 2.5 hours, poured into 2500 ml of ice-cold 2-N hydrochloric acid and exhaustively extracted with hexane. The combined hexane extracts are washed neutral with water, dried over sodium sulphate and evaporated. Vacuum distillation yields pure 3-(p-tert.amyl-phenyl)-2-methyl-allyl alcohol of boiling point 128°-133° C./0.04 Torr.

Example 19

Preparation of 3-(p-tert.-amyl-phenyl)-2,3-dimethyl-allyl bromide

A mixture of 72 g of 3-(p-tert.amyl-phenyl)-2,3-dimethyl-allyl alcohol and 7.2 ml of pyridine in 500 ml of n-pentane is cooled down to −5° C. At this temperature there are added dropwise while stirring over a period of 2 hours 40.2 g of phosphorus tribromide in 500 ml of n-pentane and the mixture is stirred at room temperature for 3 hours. The mixture is poured on to 500 g of ice and stirred up for 30 minutes. The pentane phase is separated and the aqueous phase is back-extracted with n-pentane. The combined n-pentane phases are washed neutral with saturated sodium bicarbonate solution and water, dried over sodium sulphate and evaporated. The crude 3-(p-tert.amyl-phenyl)-2,3-dimethyl-allyl bromide obtained [NMR: 60 Mc, $CDCl_3 \rightarrow 1\text{-}CH_2=3.9$ and 4.1 ppm (2s)] was used in the process without further purification.

Substituted allyl bromides of formula IIa (see Formula Scheme A and B) are thermally unstable. During the distillation of these allyl bromides partial decomposition sets in. It is accordingly advantageous to use these allyl bromides in the process without further purification.

In an analogous manner, from 3-[p-(α,α-dimethyl-benzyl)-phenyl]-2,3-dimethyl-allyl alcohol there is obtained 3-[p-(α,α-dimethyl-benzyl)-phenyl]-2,3-dimethyl-allyl bromide; NMR: 60 Mc, $CDCl_3 \rightarrow 1\text{-}CH_2 = 3.96$ and 4.16 ppm (2s), from 3-(p-cyclohexyl-phenyl)-2-methyl-allyl alcohol there is obtained 3-(p-cyclohexyl-phenyl)-2-methyl-allyl bromide of boiling point 152° C./0.01 Torr (decomposition), and from 3-(4-tert.amyl-cyclohexyl)-2-methyl-allyl alcohol there is obtained 3-(4-tert.amyl-cyclohexyl)-2-methyl-allyl bromide of boiling point 111°-115° C./0.05 Torr.

Example 20

Preparation of 3-(4-tert.-amyl-cyclohexyl)-2-methyl-acrylic acid ethyl ester

A mixture of 46.3 g of 4-tert.amyl-cyclohexane-1-carboxaldehyde, 92.3 g of (α-carbethoxy-ethylidene)-triphenyl-phosphorane and 7.6 g of benzoic acid in 250 ml of toluene is heated at reflux for 3.5 hours under nirogen gasification and the toluene is evaporated. The oily-crystalline residue is dissolved in 1600 ml of methanol/water (4:1) and exhaustively extracted with hexane. The combined hexane extracts are washed with sodium carbonate solution and water, dried over sodium sulphate and evaporated. By distillation there is obtained pure 3-(4-tert.amyl-cyclohexyl)-2-methyl-acrylic acid ethyl ester of boiling point 113°-115° C./0.03 Torr.

In an analogous manner, from p-cyclohexyl-benzaldehyde there is obtained 3-(p-cyclohexyl-phenyl)-2-methyl-acrylic acid ethyl ester of boiling point 150° C./0.03 Torr and melting point 42° C.

Example 21

Preparation of 3-(p-tert.-amyl-phenyl)-2,3-dimethyl-acrylic acid ethyl ester 261.8 g of triethyl-α-phosphonium propionate are added dropwise at room temperature to a solution of 25.3 g of sodium in 1100 ml of absolute alcohol. After stirring for 5 minutes, 190.3 g of p-tert.amyl-acetophenone are added dropwise within 15 minutes and the mixture is boiled at reflux for 24 hours. The cooled solution is evaporated, poured on to ice and exhaustively extracted with ether. The combined ether extracts are washed neutral with water, dried over sodium sulphate and evaporated. By distillation there is obtained pure 3-(p-tert.amyl-phenyl)-2,3-dimethyl-acrylic acid ethyl ester of boiling point 113° C./0.04 Torr.

In an analogous manner, from p-(α,α-dimethyl-benzyl)acetophenone there is obtained 3-[p-(α,α-dimethyl-benzyl)-phenyl]-2,3-dimethyl-acrylic acid ethyl ester; $n_D^{20} = 1.5492$.

Example 22

Preparation of 3-(p-tert.-amyl-phenyl)-2,3-dimethyl-allyl alcohol

110 G. of a 70% sodium dihydro-bis-(2-methoxyethoxy)-aluminate solution in toluene are added dropwise at 25°-30° C. over a period of 90 minutes to a solution of 85 g. of 3-(p-tert.-amyl-phenyl)-2,3-dimethyl-acrylic acid ethyl ester in 400 ml. of absolute toluene and the mixture is subsequently warmed at 40° C. for 2 hours. The mixture is then cooled down to −10° C. and treated dropwise over 300 ml. of 2 N sodium hydroxide. The toluene phase is separated and the aqueous-alkaline phase is back-extracted twice with 300 ml. of toluene. The combined toluene phases are washed neutral with water, dried over sodium sulfate and evaporated. By distillation there is obtained pure 3-(p-tert.-amyl-phenyl)-2,3-dimethyl-allyl alcohol; $n_D^{20} = 1.5311$.

In an analogous manner, from 3-(p-cyclohexyl-phenyl)-2-methyl-acrylic acid ethyl ester there is obtained 3-(p-cyclohexyl-phenyl)-2-methyl-allyl alcohol of boiling point 140° C./0.01 Torr and melting point 40.5° C., and from 3-[p-(α,α-dimethyl-benzyl)-phenyl]-2,3-dimethyl-acrylic acid ethyl ester there is obtained 3-[p-(α,α-dimethyl-benzyl)-phenyl]-2,3-dimethyl-allyl alcohol; GC: Retention time 3.8 minutes (OV-1 3%, Gaschrom Q, 80/100 mesh, 3 m×3 mm, injection and column T=250° C.).

Example 23

Preparation of 3-(p-tert.-amyl-phenyl)-2-methyl-propionaldehyde

A mixture of 172 g of α-methyl-allylidene diacetate and 160 g of p-tert.amyl-benzene is allowed to drop in to a mixture, cooled to −10° C., of 637 g of p-tert.amyl-benzene, 211 g of titanium tetrachloride and 3 g of boron trifluoride etherate while stirring over a period of 1.5 hours. The mixture is subsequently stirred at −10° C. for 45 minutes and then poured on to a mixture of 800 ml of ice-water and 140 ml of concentrated hydrochloric acid in order to hydrolyse the titanium tetrachloride. The organic layer is separated, washed neutral with water and 5% sodium bicarbonate solution, dried over sodium sulphate and the excess p-tert.amyl-benzene is distilled in a water-jet vacuum. (Boiling point 108° C./20 Torr). The residue, crude 3-(p-tert.amyl-phenyl)-2-methyl-1-propenyl acetate, is taken up in 190 ml of methanol, treated with a solution of 80 g of potassium carbonate in 145 ml of water and heated at reflux with intensive stirring until the saponification has been completed. The methanol is distilled and the organic phase is separated and distilled. There is obtained pure 3-(p-tert.amyl-phenyl)-2-methyl-propionaldehyde of boiling point 109°-111° C./0.06 Torr.

In an analogous manner, from p-neopentyl-benzene and α-methyl-allylidene diacetate there is obtained 3-(p-neopentyl-phenyl)-2-methyl-propionaldehyde of boiling point 92°-94° C./0.04 Torr, from p-(1,1-dimethyl-pentyl)-benzene and α-methyl-allylidene diacetate there is obtained 3-[p-(1,1-dimethyl-pentyl)-phenyl]-2-methyl-propionaldehyde of boiling point 107°-109° C./0.02 Torr, from p-(1,1-diethyl-propyl)-benzene and α-methyl-allylidene diacetate there is obtained 3-[p-(1,1-diethyl-propyl)-phenyl]-2-methyl-propionaldehyde of boiling point 107°-111° C./0.025 Torr, from p-tert.butyl-benzene and α-ethyl-allylidene diacetate there is obtained 3-(p-tert.butyl-phenyl)-2-ethyl-propionaldehyde of boiling point 97°-99° C./0.03 Torr, and from p-tert.butyl-benzene and α-isopropyl-allylidene diacetate there is obtained 3-(p-tert.butyl-phenyl)-2-isopropyl-propionaldehyde of boiling point 113°-115° C./0.03 Torr.

Example 24

Preparation of 3-(p-tert.-amyl-phenyl)-2-methyl-propionaldehyde

A mixture of 110 g of 3-(p-tert.amyl-phenyl)-2-methyl-acrolein, 4.75 g of 5% palladium/carbon and 0.390 g of calcium hydroxide is flushed with nitrogen and a solution of 7.6 ml of water in 285 ml of methanol is added. The mixture is hydrogenated at room temperature until 1 mol of hydrogen has been taken up. The catalyst is filtered the filtrate is evaporated and the residue is distilled. There is obtained pure 3-(p-tert.amyl-phenyl)-2-methyl-propionaldehyde of boiling point 109°-111° C./0.06 Torr.

In an analogous manner,
from 3-[p-(1-ethyl-1-methyl-butyl)-phenyl]-2-methyl-acrolein there is obtained 3-[p-(1-ethyl-1-methyl-butyl)-phenyl]-2-methyl-propionaldehyde of boiling point 105° C./0.05 Torr,
from 3-[p-(1,2-dimethyl-propyl)-phenyl]-2-methyl-acrolein there is obtained 3-[p-(1,2-dimethyl-propyl)-phenyl]-2-methyl-propionaldehyde of boiling point 80° C./0.04 Torr,
from 3-[p-(1-isopropyl-3-methyl-butyl)-phenyl]-2-methyl-acrolein there is obtained 3-[p-(1-isopropyl-3-methyl-butyl)-phenyl]-2-methyl-propionaldehyde of boiling point 95°-100° C./0.05 Torr (bulb-tube),
from 3-[p-(α,α-dimethyl-benzyl)-phenyl]-2-methyl-acrolein there is obtained 3-[p-(α,α-dimethyl-benzyl)-phenyl]-2-methyl-propionaldehyde of boiling point 165°-170° C./0.5 Torr,
from 3-[p-(2-cyclohexyl-1,1-dimethyl-ethyl)-phenyl]-2-methyl-acrolein there is obtained 3-[p-(2-cyclohexyl-1,1-dimethyl-ethyl)-phenyl]-2-methyl-propionaldehyde of boiling point 141°-143° C./0.045 Torr,
from 3-[p-(1-propyl-1-methyl-pentyl)-phenyl]-2-methyl-acrolein there is obtained 3-[p-(1-propyl-1-methyl-pentyl)-phenyl]-2-methyl-propionaldehyde of boiling point 129°-134° C./0.05 Torr,
from 3-[p-(1-cyclohexyl-1-methyl)-phenyl]-2-methyl-acrolein there is obtained 3-[p-(1-cyclohexyl-1-methyl)-phenyl]-2-methyl-propionaldehyde of boiling point 136°-141° C./0.05 Torr,
from 3-(p-benzyl-phenyl)-2-methyl-acrolein there is obtained 3-(p-benzyl-phenyl)-2-methyl-propionaldehyde of boiling point 149°-154° C./0.04 Torr,
from 3-(p-tert.butyl-phenyl)-2-octyl-acrolein there is obtained 3-(p-tert.butyl-phenyl)-2-octyl-propionaldehyde of boiling point 144°-156° C./0.028 Torr, and
from 3-(p-biphenylyl)-2-methyl-acrolein there is obtained 3-(p-biphenylyl)-2-methyl-propionaldehyde of melting point 60°-61° C.

Example 25

Preparation of 3-(p-tert.-amyl-phenyl)-2-methyl-propanol 70 g of 3-(p-tert.amyl-phenyl)-2-methyl-allyl alcohol are dissolved in 700 ml of alcohol, treated with 7 g of 5% palladium/carbon and hydrogenated until the hydrogen uptake has been completed. The catalyst is subsequently filtered and the alcohol is evaporated. By distillation there is obtained pure 3-(p-tert.amyl-phenyl)-2-methyl-propanol of boiling point 124°-129° C./0.04 Torr.

Example 26

Preparation of 3-(p-tert.-amyl-phenyl)-2-methyl-propyl bromide 32.2 g of 3-(p-tert.amyl-phenyl)-2-methyl-propanol are added dropwise at 20°-30° C. over a period of 2 hours to 21.8 g of phosphorus tribromide and the mixture is left to stand for 16 hours. The mixture is subsequently heated to 55°-60° C. for a period of 1.5 hours, cooled down to ca 10° C. and cautiously poured on to ice. The aqueous solution is exhaustively extracted with ether, the combined ether phases are washed with saturated sodium bicarbonate solution and water, dried over sodium sulphate and evaporated. By fractional distillation there is obtained pure 3-(p-tert.amyl-phenyl)-2-methyl-propyl bromide of boiling point 117°-119° C./0.035 Torr.

III. PRODUCTION OF PHARMACEUTICAL PREPARATIONS

1. Vaginal tablets

Example 27

Vaginal tablets can contain the following ingredients:

| | | |
|---|---|---|
| Active ingredient given in Table III | 100 mg | 50 mg |
| Secondary calcium phosphate diydrate | 300 mg | 400.0 mg |
| Directly pressable starch | 203 mg | 261.5 mg |
| Lactose (spray-dried) | 100 mg | 400.0 mg |
| Polyvinylpyrrolidone | 30 mg | 25.0 mg |
| Citric acid (anhydrous) | 5 mg | 5.0 mg |
| Magnesium stearate | 7 mg | 6.0 mg |
| | 745 mg | 695.0 mg |

2. Salves

Example 28

A salve for topical application can contain the following ingredients:

| | |
|---|---|
| Active ingredient given in Table III | 1.00 g |
| Cetyl alcohol | 3.60 g |
| Lanolin | 9.00 g |
| Petroleum jelly (white) | 79.00 g |
| Paraffin oil | 7.40 g |
| | 100.00 g |

3. Creams

Example 29

A cream for topical application can contain the following ingredients:

| | |
|---|---|
| Active ingredient given in Table III | 1.00 g |
| Polyoxyethylene stearate | 3.00 g |
| Stearyl alcohol | 8.00 g |
| Paraffin oil, intensively viscous | 10.00 g |
| Petroleum jelly (white) | 10.00 g |
| CARBOPOL 934 Ph | 0.30 g |
| NaOH reinst | 0.07 g |
| Water,deonised | ad 100.00 g |

I claim:

1. A compound of the formula

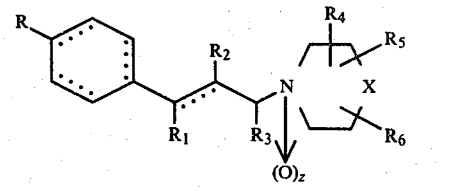
(I)

wherein R is alkyl of 4 to 12 carbon atoms, cycloalkyl of 3 to 7 carbon atoms, mono(lower alkyl)-substituted cycloalkyl of 4 to 7 carbon atoms, cycloalkylalkyl of 4 to 12 carbon atoms, phenyl, phenyl-(lower alkyl) of 7 to 12 carbon atoms, or naphthyl-(lower alkyl) of up to 12 carbon atoms in which the phenyl or naphthyl group can be mono- or di-(lower alkyl) substituted; $R_1$, and $R_3$, independently, are hydrogen or alkyl of 1 to 8 carbon atoms; $R_2$ is methyl; $R_4$, $R_5$ and $R_6$, independently, are hydrogen or alkyl of 1 to 8 carbon atoms, and two of $R_4$, $R_5$ and $R_6$ can each be bonded to the same carbon atom or can together form a fused alicyclic or aromatic 6-membered ring; provided that when R is tert.-butyl, at least one of $R_1$ and $R_3$ is alkyl of 2 to 8 carbon atoms, or at least one of $R_4$, $R_5$ and $R_6$ is alkyl of 5 to 8 carbon atoms; X is methylene or an oxygen atom; z is zero or 1; and the dotted bonds can be hydrogenated or an acid addition salt of a compound which is basic.

2. A compound, in accordance with claim 1, of the formula

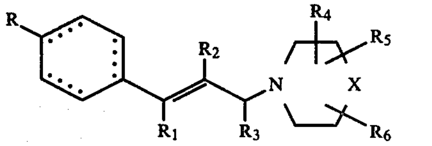
(VIIa)

wherein R is alkyl of 4 to 12 carbon atoms, cycloalkyl of 3 to 7 carbon atoms, mono(lower alkyl)-substituted cycloalkyl of 4 to 7 carbon atoms, cycloalkylalkyl of 4 to 12 carbon atoms, phenyl, phenyl-(lower alkyl) of 7 to 12 carbon atoms, or naphthyl-(lower alkyl) of up to 12 carbon atoms in which the phenyl or naphthyl group can be mono- or di-(lower alkyl) substituted; $R_1$, and $R_3$, independently, are hydrogen or alkyl of 1 to 8 carbon atoms; $R_2$ is methyl; $R_4$, $R_5$ and $R_6$, independently, are hydrogen or alkyl of 1 to 8 carbon atoms, and two of $R_4$, $R_5$ and $R_6$ can each be bonded to the same carbon atom or can together form a fused alicyclic or aromatic 6-membered ring; provided that when R is tert.-butyl, at least one of $R_1$ and $R_3$ is alkyl of 2 to 8 carbon atoms, or at least one of $R_4$, $R_5$ and $R_6$ is alkyl of 5 to 8 carbon atoms; X is methylene or an oxygen atom; and the dotted bonds can be hydrogenated or an acid addition salt of a compound which is basic.

3. A compound, in accordance with claim 1, of the formula

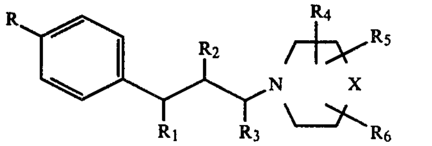
(VIIb)

wherein R is alkyl of 4 to 12 carbon atoms, cycloalkyl of 3 to 7 carbon atoms, mono(lower alkyl)-substituted cycloalkyl of 4 to 7 carbon atoms, cycloalkylalkyl of 4 to 12 carbon atoms, phenyl, phenyl-(lower alkyl) of 7 to 12 carbon atoms, or naphthyl-(lower alkyl) of up to 12 carbon atoms in which the phenyl or naphthyl group can be mono- or di-(lower alkyl)substituted; $R_1$, and $R_3$, independently, are hydrogen or alkyl of 1 to 8 carbon atoms; $R_2$ is methyl; $R_4$, $R_5$ and $R_6$, independently, are hydrogen or alkyl of 1 to 8 carbon atoms, and two of $R_4$, $R_5$ and $R_6$ can each be bonded to the same carbon atom or can together form a fused alicyclic or aromatic 6-membered ring; provided that when R is tert.-butyl, at least one of $R_1$ and $R_3$ is alkyl of 2 to 8 carbon atoms, or at least one of $R_4$, $R_5$ and $R_6$ is alkyl of 5 to 8 carbon atoms; X is methylene or an oxygen atom; or an acid addition salt of a compound which is basic.

4. A compound, in accordance with claim 1, of the formula

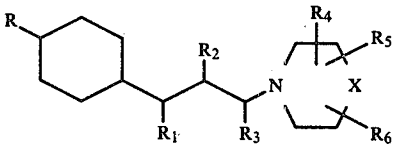
(Ia)

wherein R is alkyl of 4 to 12 carbon atoms, cycloalkyl of 3 to 7 carbon atoms, mono(lower alkyl)-substituted cycloalkyl of 4 to 7 carbon atoms, cycloalkylalkyl of 4 to 12 carbon atoms, phenyl, phenyl-(lower alkyl) of 7 to 12 carbon atoms, or naphthyl-(lower alkyl) of up to 12 carbon atoms in which the phenyl or naphthyl group can be mono- or di-(lower alkyl) substituted; $R_1$, and $R_3$, independently, are hydrogen or alkyl of 1 to 8 carbon atoms; $R_2$ is methyl; $R_4$, $R_5$ and $R_6$, independently, are hydrogen or alkyl of 1 to 8 carbon atoms, and two of $R_4$, $R_5$ and $R_6$ can each be bonded to the same carbon atom or can together form a fused alicyclic or aromatic 6-membered ring; provided that when R is tert.-butyl, at least one of $R_1$ and $R_3$ is alkyl of 2 to 8 carbon atoms, or at least one of $R_4$, $R_5$ and $R_6$ is alkyl of 5 to 8 carbon atoms; X is methylene or an oxygen atom; or an acid addition salt of a compound which is basic.

5. A compound, in accordance with claim 1, of the formula

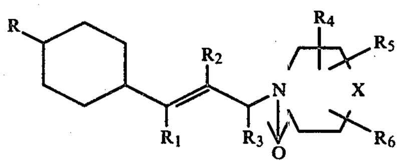
(Ib)

wherein R is alkyl of 4 to 12 carbon atoms, cycloalkyl of 3 to 7 carbon atoms, mono(lower alkyl)-substituted cycloalkyl of 4 to 7 carbon atoms, cycloalkylalkyl of 4 to 12 carbon atoms, phenyl, phenyl-(lower alkyl) of 7 to 12 carbon atoms, or naphthyl-(lower alkyl) of up to 12 carbon atoms in which the phenyl or naphthyl group can be mono- or di-(lower alkyl) substituted; $R_1$, and $R_3$, independently, are hydrogen or alkyl of 1 to 8 carbon atoms; $R_2$ is methyl; $R_4$, $R_5$ and $R_6$, independently, are hydrogen or alkyl of 1 to 8 carbon atoms, and two of $R_4$, $R_5$ and $R_6$ can each be bonded to the same carbon atom or can together form a fused alicyclic or aromatic 6-membered ring; provided that when R is tert.-butyl, at least one of $R_1$ and $R_3$ is alkyl of 2 to 8 carbon atoms, or at least one of $R_4$, $R_5$ and $R_6$ is alkyl of 5 to 8 carbon atoms; X is methylene or an oxygen atom; or an acid addition salt of a compound which is basic.

6. A compound, in accordance with claim 1, of the formula

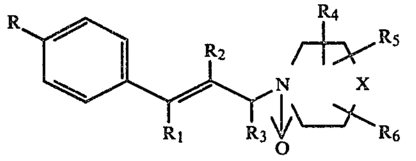

(Ic)

wherein R is alkyl of 4 to 12 carbon atoms, cycloalkyl of 3 to 7 carbon atoms, mono(lower alkyl)-substituted cycloalkyl of 4 to 7 carbon atoms, cycloalkylalkyl of 4 to 12 carbon atoms, phenyl, phenyl-(lower alkyl) of 7 to 12 carbon atoms, or naphthyl-(lower alkyl) of up to 12 carbon atoms in which the phenyl or naphthyl group can be mono- or di-(lower alkyl) substituted; $R_1$, and $R_3$, independently, are hydrogen or alkyl of 1 to 8 carbon atoms; $R_2$ is methyl; $R_4$, $R_5$ and $R_6$, independently, are hydrogen or alkyl of 1 to 8 carbon atoms, and two of $R_4$, $R_5$ and $R_6$ can each be bonded to the same carbon atom or can together form a fused alicyclic or aromatic 6-membered ring; provided that when R is tert.-butyl, at least one of $R_1$ and $R_3$ is alkyl of 2 to 8 carbon atoms, or at least one of $R_4$, $R_5$ and $R_6$ is alkyl of 5 to 8 carbon atoms; X is methylene or an oxygen atom; or an acid addition salt of a compound which is basic.

7. A compound, in accordance with claim 1, of the formula

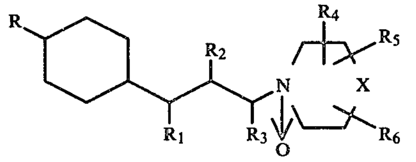

(Id)

wherein R is alkyl of 4 to 12 carbon atoms, cycloalkyl of 3 to 7 carbon atoms, mono(lower alkyl)-substituted cycloalkyl of 4 to 7 carbon atoms, cycloalkylalkyl of 4 to 12 carbon atoms, phenyl, phenyl-(lower alkyl) of 7 to 12 carbon atoms, or naphthyl-(lower alkyl) of up to 12 carbon atoms in which the phenyl or naphthyl group can be mono- or di-(lower alkyl) substituted; $R_1$, and $R_3$, independently, are hydrogen or alkyl of 1 to 8 carbon atoms; $R_2$ is methyl; $R_4$, $R_5$ and $R_6$, independently, are hydrogen or alkyl of 1 to 8 carbon atoms, and two of $R_4$, $R_5$ and $R_6$ can each be bonded to the same carbon atom or can together form a fused alicyclic or aromatic 6-membered ring; provided that when R is tert.-butyl, at least one of $R_1$ and $R_3$ is alkyl of 2 to 8 carbon atoms, or at least one of $R_4$, $R_5$ and $R_6$ is alkyl of 5 to 8 carbon atoms; X is methylene or an oxygen atom; or an acid addition salt of a compound which is basic.

8. A compound, in accordance with claim 1, of the formula

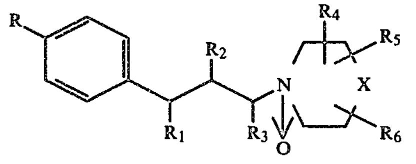

(Ie)

wherein R is alkyl of 4 to 12 carbon atoms, cycloalkyl of 3 to 7 carbon atoms, mono(lower alkyl)-substituted cycloalkyl of 4 to 7 carbon atoms, cycloalkylalkyl of 4 to 12 carbon atoms, phenyl, phenyl-(lower alkyl) of 7 to 12 carbon atoms, or naphthyl-(lower alkyl) of up to 12 carbon atoms in which the phenyl or naphthyl group can be mono- or di-(lower alkyl) substituted; $R_1$, and $R_3$, independently, are hydrogen or alkyl of 1 to 8 carbon atoms; $R_2$ is methyl; $R_4$, $R_5$ and $R_6$, independently, are hydrogen or alkyl of 1 to 8 carbon atoms, and two of $R_4$, $R_5$ and $R_6$ can each be bonded to the same carbon atom or can together form a fused alicyclic or aromatic 6-membered ring; provided that when R is tert.-butyl, at least one of $R_1$ and $R_3$ is alkyl of 2 to 8 carbon atoms, or at least one of $R_4$, $R_5$ and $R_6$ is alkyl of 5 to 8 carbon atoms; X is methylene or an oxygen atom; or an acid addition salt of a compound which is basic.

9. A compound in accordance with claim 1, 1-[3-(p-tert.amyl-phenyl)-2-methyl-propyl]-piperidine.

10. A compound in accordance with claim 1, 1-[3-(p-tert.amyl-phenyl)-2-methyl-propyl]-3-methylpiperidine.

11. A compound in accordance with claim 1, 4-[3-(p-tert.amyl-phenyl)-2-methyl-propyl]-2,6-dimethylmorpholine.

12. A compound in accordance with claim 1, 1-[3-(p-tert.amyl-phenyl)-2-methyl-propyl]-3,5-dimethylpiperidine.

13. A compound in accordance with claim 1, 1-[3-(4-tert.amyl-cyclohexyl)-2-methyl-propyl]-piperidine.

14. A compound in accordance with claim 1, 1-[3-(4-tert.amyl-cyclohexyl)-2-methyl-propyl]-3-methyl-piperidine.

15. A compound in accordance with claim 1, 1-[3-(4-tert.amyl-cyclohexyl)-2-methyl-propyl]-3,5-dimethyl-piperidine.

16. A compound in accordance with claim 1, 4-[3-(4-tert.amyl-cyclohexyl)-2-methyl-propyl]-2,6-dimethyl-morpholine.

17. A compound in accordance with claim 1, 1-[3-(p-tert.amyl-phenyl)-2-methyl-2-propenyl]-piperidine.

18. A compound in accordance with claim 1, 1-[3-(p-tert.amyl-phenyl)-2-methyl-2-propenyl]-3-methyl-piperidine.

19. A compound in accordance with claim 1, 1-[3-(p-tert.amyl-phenyl)-2-methyl-2-propenyl]-3,5-dimethyl-piperidine.

20. A compound in accordance with claim 1, 4-[3-(p-tert.amyl-phenyl)-2-methyl-2-propenyl]-2,6-dimethyl-morpholine.

21. A compound in accordance with claim 1, 1-[3-(4-tert.amyl-cyclohexyl)-2-methyl-2-propenyl]-piperidine.

22. A compound in accordance with claim 1, 1-[3-(4-tert.amyl-cyclohexyl)-2-methyl-2-propenyl]-3-methyl-piperidine.

23. A compound in accordance with claim 1, 1-[3-(4-tert.amyl-cyclohexyl)-2-methyl-2-propenyl]-3,5-dimethylpiperidine.

24. A compound in accordance with claim 1, 4-[3-(4-tert.amyl-cyclohexyl)-2-methyl-2-propenyl]-2,6-dimethylmorpholine.

25. A compound in accordance with claim 1, 1-[3-(p-tert.amyl-phenyl)-2,3-dimethyl-2-propenyl]-piperidine.

26. A compound in accordance with claim 1, 1-[3-(p-tert.amyl-phenyl)-2,3-dimethyl-2-propenyl]-3-methyl-piperidine.

27. A compound in accordance with claim 1, 1-[3-(p-tert.amyl-phenyl)-2,3-dimethyl-2-propenyl]-3,5-dimethylpiperidine.

28. A compound in accordance with claim 1, 4-[3-(p-tert.amyl-phenyl)-2,3-dimethyl-2-propenyl]-2,6-dimethyl-morpholine.

29. A compound in accordance with claim 1, 1-[3-(p-tert.amyl-phenyl)-2,3-dimethyl-propyl]-piperidine.

30. A compound in accordance with claim 1, 1-[3-(p-tert.amyl-phenyl)-2,3-dimethyl-propyl]-3-methylpiperidine.

31. A compound in accordance with claim 1, 1-[3-(p-tert.amyl-phenyl)-2,3-dimethyl-propyl]-3,5-dimethyl-piperidine.

32. A compound in accordance with claim 1, 4-[3-(p-tert.amyl-phenyl)-2,3-dimethyl-propyl]-2,6-dimethyl-morpholine.

33. A compound in accordance with claim 1, 1-[3-(p-neopentyl-phenyl)-2-methyl-propyl]-piperidine.

34. A compound in accordance with claim 1, 1-[3-(p-neopentyl-phenyl)-2-methyl-propyl]-3-methylpiperidine.

35. A compound in accordance with claim 1, 1-[3-(p-isobutyl-phenyl)-2-methyl-propyl]-piperidine.

36. A compound in accordance with claim 1, 4-[3-(p-isobutyl-phenyl)-2-methyl-propyl]-2,6-dimethylmorpholine.

37. A compound in accordance with claim 1, 4-[3-(p-neopentyl-phenyl)-2-methylpropyl]-2,6-dimethylmorpholine.

38. A compound in accordance with claim 1, 1-{3-[p-(1,1-dimethyl-pentyl)phenyl]-2-methyl-propyl}-piperidine.

39. A compound in accordance with claim 1, 1-{3-[p-(1,1-dimethyl-pentyl)phenyl]-2-methyl-propyl}-3-methylpiperidine.

40. A compound in accordance with claim 1, 1-{3-[p-(1,1-diethyl-propyl)-phenyl-2-methyl-propyl}-piperidine.

41. A compound in accordance with claim 1, 1-{3-[p-(1,1-diethyl-propyl)-phenyl]-2-methyl-propyl}-3-methylpiperidine.

42. A compound in accordance with claim 1, 1-(3-p-biphenylyl-2-methyl-propyl)-piperidine.

43. A compound in accordance with claim 1, 1-(3-p-biphenylyl-2-methyl-propyl)-3-methylpiperidine.

44. A compound in accordance with claim 1, 1-[2-(p-tert.butyl-benzyl)-3-methylbutyl]-piperidine.

45. A compound in accordance with claim 1, 1-[2-(p-tert.butyl-benzyl)-3-methylbutyl]-3-methylpiperidine.

46. A compound in accordance with claim 1, 1-[2-(p-tert.butyl-benzyl)-decyl]piperidine.

47. A compound in accordance with claim 1, 1-[2-(p-tert.butyl-benzyl)-decyl]-3-methylpiperidine.

48. A compound in accordance with claim 1, 1-[3-(p-cyclohexyl-phenyl)-2-methyl-2-propenyl]-piperidine.

49. A compound in accordance with claim 1, 1-{3-[p-(1-ethyl-methyl-butyl)phenyl]-2-methylpropyl}-piperidine.

50. A compound in accordance with claim 1, 4-{3-[p-(1-ethyl-1-methyl-butyl)phenyl]-2-methylpropyl}-2,6-dimethylmorpholine.

51. A compound in accordance with claim 1, 1-{3-[p-(1,2-dimethyl-propyl)phenyl]-2-methyl-propyl}-piperidine.

52. A compound in accordance with claim 1, 4-{3-[p-(1,2-dimethyl-propyl)phenyl]-2-methyl-propyl}-2,6-dimethylmorpholine.

53. A compound in accordance with claim 1, 4-{3-[p-(1-isopropyl-3-methylbutyl)-phenyl]-2-methyl-propyl}-2,6-dimethylmorpholine.

54. A compound in accordance with claim 1, 1-{3-[p-(1-isopropyl-3-methylbutyl)phenyl]-2-methyl-propyl}-piperidine.

55. A compound in accordance with claim 1, 1-{3-[p-(α,α-dimethyl-benzyl)phenyl]-2-methyl-propyl}-piperidine.

56. A compound in accordance with claim 1, 1-{3-[p-(α,α-dimethyl-benzyl)phenyl]-2-methyl-propyl}-3-methylpiperidine.

57. A compound in accordance with claim 1, 4-{3-[p-(α,α-dimethyl-benzyl)phenyl]-2-methyl-propyl}-2,6-dimethyl-morpholine.

58. A compound in accordance with claim 1, 1-{3-[p-(α,α-dimethyl-benzyl)phenyl]-2,3-dimethyl-2-propenyl}-3,5-dimethylpiperidine.

59. A compound in accordance with claim 1, 1-{3-[p-(α,α-dimethyl-benzyl)phenyl]-2,3-dimethyl-propyl}-3,5-dimethylpiperidine.

60. A compound in accordance with claim 1, 1-{3-[p-(2-cyclohexyl-1,1-dimethylethyl)-phenyl]-2-methyl-propyl}-piperidine.

61. A compound in accordance with claim 1, 4-{3-[p-2-cyclohexyl-1,1-dimethylethyl)-phenyl]-2-methyl-propyl}-2,6-dimethylmorpholine.

62. A compound in accordance with claim 1, 1-{3-[p-(1-propyl-1-methyl-pentyl)phenyl]-2-methyl-propyl}-piperidine.

63. A compound in accordance with claim 1, 1-{3-[p-(1-propyl-1-methyl-pentyl)phenyl]-2-methyl-propyl}-3,5-dimethylpiperidine.

64. A compound in accordance with claim 1, 4-{3-[p-(1-propyl-1-methyl-pentyl)phenyl]-2-methyl-propyl}-2,6-dimethyl-morpholine.

65. A compound in accordance with claim 1, 1-{3-[4-(1-cyclohexyl-1-methylethyl)-cyclohexyl]-2-methyl-propyl}-piperidine.

66. A compound in accordance with claim 1, 4-{3-[4-(1-cyclohexyl-1-methylethyl)-cyclohexyl]-2-methyl-propyl}-2,6-dimethylmorpholine.

67. A compound in accordance with claim 1, 1-{3-[p-(1-cyclohexyl-1-methyl)phenyl]-2-methyl-propyl}-piperidine.

68. A compound in accordance with claim 1, 1-{3-[p-(1-cyclohexyl-1-methyl)phenyl]-2-methyl-propyl}-3,5-dimethylpiperidine.

69. A compound in accordance with claim 1, 4-{3-[p-(1-cyclohexyl-1-methyl)phenyl]-2-methyl-propyl}-2,6-dimethylmorpholine.

70. A compound in accordance with claim 1, 1-[3-(4-biphenylyl)-2-methylpropyl]-3-ethylpiperidine.

71. A compound in accordance with claim 1, 4-[3-(4-biphenylyl)-2-methylpropyl]-2,6-dimethylmorpholine.

72. A compound in accordance with claim 1, 1-[3-(p-benzyl-phenyl)-2-methylpropyl]-piperidine.

73. A compound in accordance with claim 1, 4-[3-(p-benzyl-phenyl)-2-methylpropyl]-2,6-dimethylmorpholine.

74. A compound in accordance with claim 1, 1-[3-(p-tert.amyl-phenyl)-2-methylpropyl]-piperidine-1-oxide.

75. An agricultural fungicidal composition comprising an effective amount of at least one compound of the formula

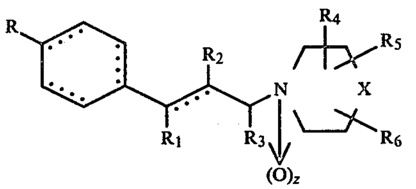

(I)

wherein R is alkyl of 4 to 12 carbon atoms, cycloalkyl of 3 to 7 carbon atoms, mono(lower alkyl)-substituted cycloalkyl of 4 to 7 carbon atoms, cycloalkylalkyl of 4 to 12 carbon atoms, phenyl, phenyl-(lower alkyl) of 7 to 12 carbon atoms, or naphthyl-(lower alkyl) of up to 12 carbon atoms in which the phenyl or naphthyl group can be mono- or di-(lower alkyl) substituted; $R_1$, and $R_3$, independently, are hydrogen or alkyl of 1 to 8 carbon atoms; $R_2$ is methyl; $R_4$, $R_5$ and $R_6$, independently, are hydrogen or alkyl of 1 to 8 carbon atoms, and two of $R_4$, $R_5$ and $R_6$ can each be bonded to the same carbon atom or can together form a fused alicyclic or aromatic 6-membered ring; provided that when R is tert.-butyl, at least one of $R_1$ and $R_3$ is alkyl of 2 to 8 carbon atoms, or at least one of $R_4$, $R_5$ and $R_6$ is alkyl of 5 to 8 carbon atoms; X is methylene or an oxygen atom; z is zero or 1; and the dotted bonds can be hydrogenated or an acid addition salt of a compound which is basic.

76. An agricultural fungicidal composition, in accordance with claim 75, which contains 1-[3-(p-tert.amylphenyl)-2-methyl-propyl]-piperidine.

77. An agricultural fungicidal composition, in accordance with claim 75, which contains 1-[3-(p-tert.amylphenyl)-2-methyl-propyl]-3-methylpiperidine.

78. An agricultural fungicidal composition, in accordance with claim 75, which contains 4-[3-(p-tert.amylphenyl)-2-methyl-propyl]-2,6-dimethylmorpholine.

79. An agricultural fungicidal composition, in accordance with claim 75, which contains 1-[3-(p-tert.amylphenyl)-2-methyl-propyl]-3,5-dimethylpiperidine.

80. An agricultural fungicidal composition, in accordance with claim 75, which contains 1-[3-(4-tert.amylcyclohexyl)-2-methyl-propyl]-piperidine.

81. An agricultural fungicidal composition, in accordance with claim 75, which contains 1-[3-(4-tert.amylcyclohexyl)-2-methyl-propyl]-3-methylpiperidine.

82. An agricultural fungicidal composition, in accordance with claim 75, which contains 1-[3-(4-tert.amylcyclohexyl)-2-methyl-propyl]-3,5-dimethylpiperidine.

83. An agricultural fungicidal composition, in accordance with claim 75, which contains 4-[3-(4-tert.amylcyclohexyl)-2-methyl-propyl]-2,6-dimethylmorpholine.

84. An agricultural fungicidal composition, in accordance with claim 75, which contains 1-[3-(p-tert.amylphenyl)-2-methyl-2-propenyl]-piperidine.

85. An agricultural fungicidal composition, in accordance with claim 75, which contains 1-[3-(p-tert.amylphenyl)-2-methyl-2-propenyl]-3-methyl-piperidine.

86. An agricultural fungicidal composition, in accordance with claim 75, which contains 1-[3-(p-tert.amylphenyl)-2-methyl-2-propenyl]-3,5-dimethylpiperidine.

87. An agricultural fungicidal composition, in accordance with claim 75, which contains 4-[3-(p-tert.amylphenyl)-2-methyl-2-propenyl]-2,6-dimethylmorpholine.

88. An agricultural fungicidal composition, in accordance with claim 75, which contains 1-[3-(4-tert.amylcyclohexyl)-2-methyl-2-propenyl]-piperidine.

89. An agricultural fungicidal composition, in accordance with claim 75, which contains 1-[3-(4-tert.amylcyclohexyl)-2-methyl-2-propenyl]-3-methylpiperidine.

90. An agricultural fungicidal composition, in accordance with claim 75, which contains 1-[3-(4-tert.amylcyclohexyl)-2-methyl-2-propenyl]-3,5-dimethylpiperidine.

91. An agricultural fungicidal composition, in accordance with claim 75, which contains 4-[3-(4-tert.amylcyclohexyl)-2-methyl-2-propenyl]-2,6-dimethylmorpholine.

92. An agricultural fungicidal composition, in accordance with claim 75, which contains 1-[3-(p-tert.amylphenyl)-2,3-dimethyl-2-propenyl]-piperidine.

93. An agricultural fungicidal composition, in accordance with claim 75, which contains 1-[3-(p-tert.amylphenyl)-2,3-dimethyl-2-propenyl]-3-methylpiperidine.

94. An agricultural fungicidal composition, in accordance with claim 75, which contains 1-[3-(p-tert.amylphenyl)-2,3-dimethyl-2-propenyl]-3,5-dimethylpiperidine.

95. An agricultural fungicidal composition, in accordance with claim 75, which contains 4-[3-(p-tert.amylphenyl)-2,3-dimethyl-2-propenyl]-2,6-dimethylmorpholine.

96. An agricultural fungicidal composition, in accordance with claim 75, which contains 1-[3-(p-tert.amylphenyl)-2,3-dimethyl-propyl]-piperidine.

97. An agricultural fungicidal composition, in accordance with claim 75, which contains 1-[3-(p-tert.amylphenyl)-2,3-dimethyl-propyl]-3-methylpiperidine.

98. An agricultural fungicidal composition, in accordance with claim 75, which contains 1-[3-(p-tert.amylphenyl)-2,3-dimethyl-propyl]-3,5-dimethylpiperidine.

99. An agricultural fungicidal composition, in accordance with claim 75, which contains 4-[3-(p-tert.amylphenyl)-2,3-dimethyl-propyl]-2,6-dimethylmorpholine.

100. An agricultural fungicidal composition, in accordance with claim 75, which contains 1-[3-(p-neopentylphenyl)-2-methyl-propyl]-piperidine.

101. An agricultural fungicidal composition, in accordance with claim 75, which contains 1-[3-(p-neopentylphenyl)-2-methyl-propyl]-3-methylpiperidine.

102. An agricultural fungicidal composition, in accordance with claim 75, which contains 1-[3-(p-isobutylphenyl)-2-methyl-propyl]-piperidine.

103. An agricultural fungicidal composition, in accordance with claim 75, which contains 4-[3-(p-isobutylphenyl)-2-methyl-propyl]-2,6-dimethylmorpholine.

104. An agricultural fungicidal composition, in accordance with claim 75, which contains 4-[3-(p-neopentylphenyl)-2-methyl-propyl]-2,6-dimethylmorpholine.

105. An agricultural fungicidal composition, in accordance with claim 75, which contains 1-{3-[p-(1,1-dimethyl-pentyl)-phenyl]-2-methyl-propyl}-piperidine.

106. An agricultural fungicidal composition, in accordance with claim 75, which contains 1-{3-[p-(1,1-dimethyl-pentyl)-phenyl]-2-methyl-propyl}-3-methylpiperidine.

107. An agricultural fungicidal composition, in accordance with claim 75, which contains 1-{3-[p-(1,1-diethyl-propyl)-phenyl]-2-methyl-propyl}-piperidine.

108. An agricultural fungicidal composition, in accordance with claim 75, which contains 1-{3-[p-(1,1-diethyl-propyl)-phenyl]-2-methyl-propyl}-3-methylpiperidine.

109. An agricultural fungicidal composition, in accordance with claim 75, which contains 1-(3-p-biphenylyl-2-methyl-propyl)-piperidine.

110. An agricultural fungicidal composition, in accordance with claim 75, which contains 1-(3-p-biphenylyl-2-methyl-propyl)-3-methylpiperidine.

111. An agricultural fungicidal composition, in accordance with claim 75, which contains 1-[2-(p-tert.butyl-benzyl)-3-methyl-butyl]-piperidine.

112. An agricultural fungicidal composition, in accordance with claim 75, which contains 1-[2-(p-tert.butyl-benzyl)-3-methyl-butyl]-3-methylpiperidine.

113. An agricultural fungicidal composition, in accordance with claim 75, which contains 1-[2-(p-tert.butyl-benzyl)-decyl]-piperidine.

114. An agricultural fungicidal composition, in accordance with claim 75, which contains 1-[2-(p-tert.butyl-benzyl)-decyl]-3-methylpiperidine.

115. An agricultural fungicidal composition, in accordance with claim 75, which contains 1-[3-(p-cyclohexyl-phenyl)-2-methyl-2-propenyl]-piperidine.

116. An agricultural fungicidal composition, in accordance with claim 75, which contains 1-{3-[p-(1-ethyl-1-butyl)-phenyl]-2-methyl-propyl}-piperidine.

117. An agricultural fungicidal composition, in accordance with claim 75, which contains 4-{3-[p-(1-ethyl-1-methyl-butyl)-phenyl]-2-methyl-propyl}-2,6-dimethyl-morpholine.

118. An agricultural fungicidal composition, in accordance with claim 75, which contains 1-{3-[p-(1,2-dimethyl-propyl)-phenyl]-2-methyl-propyl}-piperidine.

119. An agricultural fungicidal composition, in accordance with claim 75, which contains 4-{3-[p-(1,2-dimethyl-propyl)-phenyl]-2-methyl-propyl}-2,6-dimethylmorpholine.

120. An agricultural fungicidal composition, in accordance with claim 75, which contains 4-{3-[p-(1-isopropyl-3-methyl-butyl)-phenyl]-2-methyl-propyl}-2,6-dimethylmorpholine.

121. An agricultural fungicidal composition, in accordance with claim 75, which contains 1-{3-[p-(1-isopropyl-3-methyl-butyl)-phenyl]-2-methyl-propyl}-piperidine.

122. An agricultural fungicidal composition, in accordance with claim 75, which contains 1-{3-[p-(α,α-dimethyl-benzyl)-phenyl]-2-methyl-propyl}-piperidine.

123. An agricultural fungicidal composition, in accordance with claim 75, which contains 1-{3-[p-(α,α-dimethyl-benzyl)-phenyl]-2-methyl-propyl}-3-methyl-piperidine.

124. An agricultural fungicidal composition, in accordance with claim 75, which contains 4-{3-[p-(α,α-dimethyl-benzyl)-phenyl]-2-methyl-propyl}-2,6-dimethylmorpholine.

125. An agricultural fungicidal composition, in accordance with claim 75, which contains 1-{3-[p-(α,α-dimethyl-benzyl)-phenyl]-2,3-dimethyl-2-propenyl}-3,5-dimethylpiperidine.

126. An agricultural fungicidal composition, in accordance with claim 75, which contains 1-{3-[p-(α,α-dimethyl-benzyl)-phenyl]-2,3-dimethyl-propyl}-3,5-dimethylpiperidine.

127. An agricultural fungicidal composition, in accordance with claim 75, which contains 1-{3-[p-(2-cyclohexyl-1,1-dimethyl-ethyl)-phenyl]-2-methyl-propyl}-piperidine.

128. An agricultural fungicidal composition, in accordance with claim 75, which contains 4-{3-[p-(2-cyclohexyl-1,1-dimethyl-ethyl)-phenyl]-2-methyl-propyl}-2,6-dimethylmorpholine.

129. An agricultural fungicidal composition, in accordance with claim 75, which contains 1-{3-[p-(1-propyl-1-methyl-pentyl)-phenyl]-2-methyl-propyl}-piperidine.

130. An agricultural fungicidal composition, in accordance with claim 75, which contains 1-{3-[p-(1-propyl-1-methyl-pentyl)-phenyl]-2-methyl-propyl}-3,5-dimethylpiperidine.

131. An agricultural fungicidal composition, in accordance with claim 75, which contains 4-{3-[p-(1-propyl-1-methyl-pentyl)-phenyl]-2-methyl-propyl}-2,6-dimethylmorpholine.

132. An agricultural fungicidal composition, in accordance with claim 75, which contains 1-{3-[4-(1-cyclohexyl-1-methyl-ethyl)-cyclohexyl]-2-methyl-propyl}-piperidine.

133. An agricultural fungicidal composition, in accordance with claim 75, which contains 4-{3-[4-(1-cyclohexyl-1-methyl-ethyl)-cyclohexyl]-2-methyl-propyl}-2,6-dimethylmorpholine.

134. An agricultural fungicidal composition, in accordance with claim 75, which contains 1-{3-[p-(1-cyclohexyl-1-methyl)-phenyl]-2-methyl-propyl}-piperidine.

135. An agricultural fungicidal composition, in accordance with claim 75, which contains 1-{3-[p-(1-cyclohexyl-1-methyl)-phenyl]-2-methyl-propyl}-3,5-dimethylpiperidine.

136. An agricultural fungicidal composition, in accordance with claim 75, which contains 4-{3-[p-(1-cyclohexyl-1-methyl)-phenyl]-2-methyl-propyl}-2,6-dimethylmorpholine.

137. An agricultural fungicidal composition, in accordance with claim 75, which contains 1-[3-(4-biphenylyl)-2-methyl-propyl]-3-ethylpiperidine.

138. An agricultural fungicidal composition, in accordance with claim 75, which contains 4-[3-(4-biphenylyl)-2-methyl-propyl]-2,6-dimethylmorpholine.

139. An agricultural fungicidal composition, in accordance with claim 75, which contains 1-[3-(p-benzyl-phenyl)-2-methyl-propyl]-piperidine.

140. An agricultural fungicidal composition, in accordance with claim 75, which contains 4-[3-(p-benzyl-phenyl)-2-methyl-propyl]-2,6-dimethylmorpholine.

* * * * *